US010352011B2

(12) United States Patent
Erickson et al.

(10) Patent No.: US 10,352,011 B2
(45) Date of Patent: Jul. 16, 2019

(54) HUMECTANT COMPOSITIONS THAT EFFECTIVELY INCREASE MOISTURE RETENTION IN SOIL AND ASSOCIATED METHODS FOR IDENTIFYING SAME

(71) Applicant: BASF SE, Ludwigshafen (DE)

(72) Inventors: John P. Erickson, Southgate, MI (US); Yeonsuk Roh, Canton, MI (US); Daniel Niedzwiecki, Trenton, MI (US)

(73) Assignee: BASF SE, Ludwigshafen am Rhein (DE)

( * ) Notice: Subject to any disclaimer, the term of this patent is extended or adjusted under 35 U.S.C. 154(b) by 170 days.

(21) Appl. No.: 14/208,589

(22) Filed: Mar. 13, 2014

(65) Prior Publication Data

US 2014/0270984 A1 Sep. 18, 2014

Related U.S. Application Data

(60) Provisional application No. 61/779,486, filed on Mar. 13, 2013.

(51) Int. Cl.
E02D 3/00 (2006.01)
C08G 65/26 (2006.01)
(Continued)

(52) U.S. Cl.
CPC ............... *E02D 3/00* (2013.01); *B01J 20/26* (2013.01); *C08F 283/06* (2013.01);
(Continued)

(58) Field of Classification Search
CPC ........ E02D 3/00; G01N 33/246; C09K 17/18; B01J 20/26; C08G 65/2612; C08G 65/2609; C08L 71/02; C08F 283/06
See application file for complete search history.

(56) References Cited

U.S. PATENT DOCUMENTS 2,425,845 A * 8/1947 Toussaint ........... C08G 65/2609
252/73
3,022,335 A 2/1962 Lundsted
(Continued)

FOREIGN PATENT DOCUMENTS

CN 1475516 A 2/2004
CN 1880355 A 12/2006
(Continued)

OTHER PUBLICATIONS

International Search Report for Application No. PCT/US2014/025504 dated Sep. 25, 2014, 5 pages.
(Continued)

Primary Examiner — Peter F Godenschwager
Assistant Examiner — Andrew J. Oyer
(74) Attorney, Agent, or Firm — DLA Piper LLP (US)

(57) ABSTRACT

A method for increasing moisture retention in a soil includes applying an effective amount of an effective humectant composition to the soil. The effective humectant composition is identified by determining the average moisture content of the soil for the humectant compositions applied at a minimum humectant concentration level, a maximum humectant concentration level, and at a first concentration level between the minimum and the maximum humectant concentration level. An average slope curve is generated by plotting the determined average moisture content of the soil for each applied humectant concentration levels from the minimum humectant concentration level to the maximum humectant concentration level. An effective humectant composition is determined when the generated average slope curve provides an increasing average moisture content along the entirety of a length of the generated average slope curve and when the generated average slope curve has a p value of 0.05 or less.

15 Claims, 20 Drawing Sheets

(51) Int. Cl.
*C08L 71/02* (2006.01)
*C08F 283/06* (2006.01)
*C09K 17/18* (2006.01)
*G01N 33/24* (2006.01)
*B01J 20/26* (2006.01)

(52) U.S. Cl.
CPC ..... *C08G 65/2609* (2013.01); *C08G 65/2612* (2013.01); *C08L 71/02* (2013.01); *C09K 17/18* (2013.01); *G01N 33/246* (2013.01)

(56) References Cited

U.S. PATENT DOCUMENTS

| | | | |
|---|---|---|---|
| 3,461,086 A * | 8/1969 | Thurman, Jr. | C08G 18/4804 521/160 |
| 3,956,410 A | 5/1976 | Koff | |
| 4,272,394 A | 6/1981 | Kaneko | |
| 4,317,940 A | 3/1982 | Scardera et al. | |
| 4,411,810 A | 10/1983 | Dutton et al. | |
| 4,533,485 A | 8/1985 | O'Connor et al. | |
| 4,836,951 A | 6/1989 | Totten et al. | |
| 4,925,988 A | 5/1990 | Licht et al. | |
| 5,120,708 A | 6/1992 | Melear et al. | |
| 5,142,020 A | 8/1992 | Kud et al. | |
| 5,187,191 A | 2/1993 | Often et al. | |
| 5,863,521 A * | 1/1999 | Schaefer | A61K 8/22 424/49 |
| 6,079,153 A | 6/2000 | Templeton | |
| 7,288,581 B2 | 10/2007 | Ferrall et al. | |
| 7,399,730 B2 | 7/2008 | Kostka et al. | |
| 7,541,386 B2 * | 6/2009 | Kostka | C09K 17/16 47/58.1 R |
| 7,705,616 B2 | 4/2010 | Hawkins | |
| 2003/0073583 A1 | 4/2003 | Kostka et al. | |
| 2008/0172937 A1 * | 7/2008 | Palmer | C05G 3/06 47/58.1 SC |
| 2012/0128888 A1 * | 5/2012 | Roeger-Goepfert | C25D 3/38 427/457 |

FOREIGN PATENT DOCUMENTS

| | | |
|---|---|---|
| CN | 101080479 A | 11/2007 |
| CN | 101613603 A | 12/2009 |
| JP | H05-125352 | 5/1993 |
| JP | 2008-239447 A | 10/2008 |
| WO | WO 2011012462 A2 * | 2/2011 ............ C25D 3/38 |

OTHER PUBLICATIONS

Andry, H. et al., "Water Retention, Hydraulic Conductivity of Hydrophilic Polymers in Sandy Soil as Affected by Temperature and Water Quality", Journal of Hydrology 373 (2009), pp. 177-183.

Leciejewski, Piotr, "The Effect of Hydrogel Additives on the Water Retention Curve of Sandy Soil from Forest Nursery in Julinek", Journal of Water and Land Development, J. Water Land Dev. No. 13a, 2009, pp. 239-247.

Vijayalakshmi, M. et al., "Effect of Polymers on Moisture Retention and Soil Water Holding Capacity", Karnataka J. Agric. Sci. 25 (4) (2012), pp. 469-471.

English language abstract and machine-assisted English translation for CN 1475516 extracted from espacenet.com database on Oct. 4, 2017, 21 pages.

English language abstract and machine-assisted English translation for CN 1880355 extracted from espacenet.com database on Oct. 4, 2017, 21 pages.

English language abstract for CN 101080479 extracted from espacenet.com database on Oct. 4, 2017, 1 page.

English language abstract and machine-assisted English translation for CN 101613603 extracted from espacenet.com database on Oct. 4, 2017, 13 pages.

Third Office Action from corresponding Chinese Patent Application No. 201480022575.1 and its English translation; dated Mar. 5, 2018.

Notification of Reasons for Refusal from corresponding Japanese Patent Application No. 2016-501863 and its English translation; dated Jan. 15, 2018.

Office Action from corresponding European Patent Application No. 14717592.1 dated Nov. 26, 2018.

First Examination Report from counterpart Indian Application No. 5488/CHENP/2015 dated Apr. 11, 2019.

\* cited by examiner

Example A- Dinuba Soil

Example A- Los Banos Soil

Example A- Lubbock Soil

Example A- Nebraska Soil

Example B- Dinuba Soil

Example B- Los Banos Soil

Example B- Lubbock Soil

Example B- Nebraska Soil

Example C- Dinuba Soil

Example C- Los Banos Soil

Example D- Dinuba Soil

Example D- Los Banos Soil

Example D- Lubbock Soil

Example D- Nebraska Soil

Example E- Dinuba Soil

Example E- Los Banos Soil

Example E- Lubbock Soil

Example E- Nebraska Soil

Example F – Dinuba Soil

Example F – Los Banos Soil

Example F – Lubbock Soil

Example F – Nebraska Soil

Example G – Dinuba Soil

Example G – Los Banos Soil

Example G – Lubbock Soil

Example G – Nebraska Soil

Example H – Dinuba Soil

Example H – Los Banos Soil

Example H – Lubbock Soil

Example H – Nebraska Soil

Example I – Dinuba Soil

Example I – Los Banos Soil

Example I – Lubbock Soil

Example I – Nebraska Soil

HUMECTANT COMPOSITIONS THAT EFFECTIVELY INCREASE MOISTURE RETENTION IN SOIL AND ASSOCIATED METHODS FOR IDENTIFYING SAME

RELATED APPLICATIONS

This application claims priority to and all advantages of U.S. Provisional Patent Application No. 61/779,486, which was filed on Mar. 13, 2013.

BACKGROUND OF THE INVENTION

1. Field of the Invention

The instant invention generally relates methods for increasing moisture retention in soils, and more specifically relates to methods for identifying humectant compositions that effectively increase the moisture retention rate of soils.

2. Description of the Related Art

Control of water evaporation is an important consideration for many applications, especially in the agricultural, landscaping, and construction industries. As one example, top spray irrigation methods in the agricultural and landscaping industries generally have poor efficiency, which is attributable to loss of water through evaporation. Thus, it is desirable to minimize evaporation to increase the availability of irrigation water and "naturally sourced" water, such as rain and dew, for uptake by botanical articles such as agricultural crops, grass, and decorative plants. In the construction industry, airborne dust is often annoying and can cause health problems or damage to machinery. Water is often used for dust control at construction sites or on dirt roads. However, atmospheric dust may become a problem upon drying of wetted surfaces such that it is desirable to minimize evaporation of the water to lengthen the time period over which dust control treatment is effective.

Methods of slowing water evaporation, especially for landscaping applications, have been explored in the past. For example, lawn seed compositions including a combination of absorbent fibrous materials and grass seed have been employed, with the absorbent fibrous materials serving to slow evaporation of water to promote growth of the grass seed. However, application of such combinations can be cumbersome, with wet application of such compositions being hindered by difficult pumpability due to the presence of the absorbent fibrous materials.

Absorbent polymers have previously been developed. For example, super absorbent polymers (often referred to in the art as SAPs) are well-known for various applications and have the ability to absorb many times their weight in water. SAPs are available commercially in a variety of chemical forms, including substituted and unsubstituted natural and synthetic polymers, such as hydrolysis products of starch acrylonitrile graft polymers, carboxymethylcellulose, cross-linked polyacrylates, sulfonated polystyrenes, hydrolyzed polyacrylamides, polyvinyl alcohols, polyvinylpyrrolidones, polyacrylonitriles and the like. SAPs are known for use in various applications such as in sanitary articles or other applications where the function of liquid absorption is of primary focus. However, many SAPs do not readily release liquid once the liquid is absorbed such that many SAPs may not be ideal for hydration applications in which there is a desire to slow evaporation of liquid while still providing for release of the liquid into the surrounding environment.

Humectant compositions of isocyanates and polyester monols have also been utilized in the art as lubricants, surfactants, and thickeners within resin systems that include other urethane-containing compounds. Additionally, polyester monols have been utilized in isocyanate prepolymers, in which the monols are utilized to cap polyisocyanates with isocyanate groups remaining in the isocyanate prepolymer to prevent further reaction.

In view of the foregoing, there remains an opportunity to provide a method for increasing moisture retention in soil for determining novel compositions that increase moisture retention across a range of application concentrations.

SUMMARY OF THE INVENTION AND ADVANTAGES

The present invention provides a method for increasing moisture retention in a soil by applying an effective amount of an effective humectant composition to the soil. The effective humectant composition is identified by applying the humectant composition to the soil at a minimum humectant concentration level, at a first humectant concentration level greater than the minimum humectant concentration level, and at a maximum humectant concentration level greater than first humectant concentration level and determining the average moisture content at each applied humectant concentration level. The method further includes generating an average slope curve by plotting the average moisture content of the soil at each of the applied humectant concentration levels. The method further includes determining that the humectant composition is an effective humectant composition for increasing moisture retention in the soil when the generated average slope curve provides an increasing average moisture content along the entirety of a length of the average slope curve from the minimum humectant concentration level to the maximum humectant concentration level and when the generated average slope curve has a p value of 0.05 or less.

In related embodiments, this method can be extended to identify a particular humectant composition that can be effective over a larger subset of similar soils or over an entire class of similar soils. For example, in certain embodiments, polyol compositions developed by the above method have been found to be effective in increasing the moisture retention levels over most soil types found throughout the world as represented by four representative soil types found in various locations in the United States.

The present invention also provides effective humectant compositions for application to one or more soils and treated soils including the effective humectant compositions.

The method of the present invention provides a statistically sound and repeatable method for identifying humectant compositions that can be effective at increasing moisture retention for a particular soil or closely related group of soils.

BRIEF DESCRIPTION OF THE DRAWINGS

Other advantages of the present invention will be readily appreciated, as the same becomes better understood by reference to the following detailed description when considered in connection with the accompanying drawings.

DETAILED DESCRIPTION OF THE INVENTION

Figure 1:
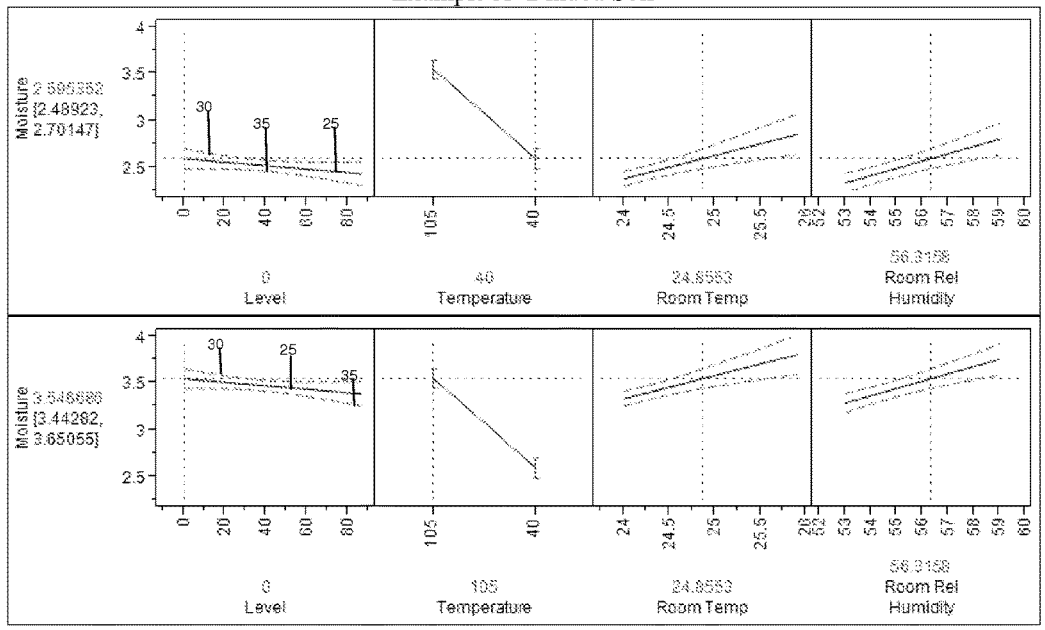
FIGS. 1 and 2 illustrate Fit Model Analysis graphs plotting moisture content for one humectant composition (Sample A) in four representative soil types utilizing two Mettler moisture balances in accordance with the method of the present invention.
Figure 1:
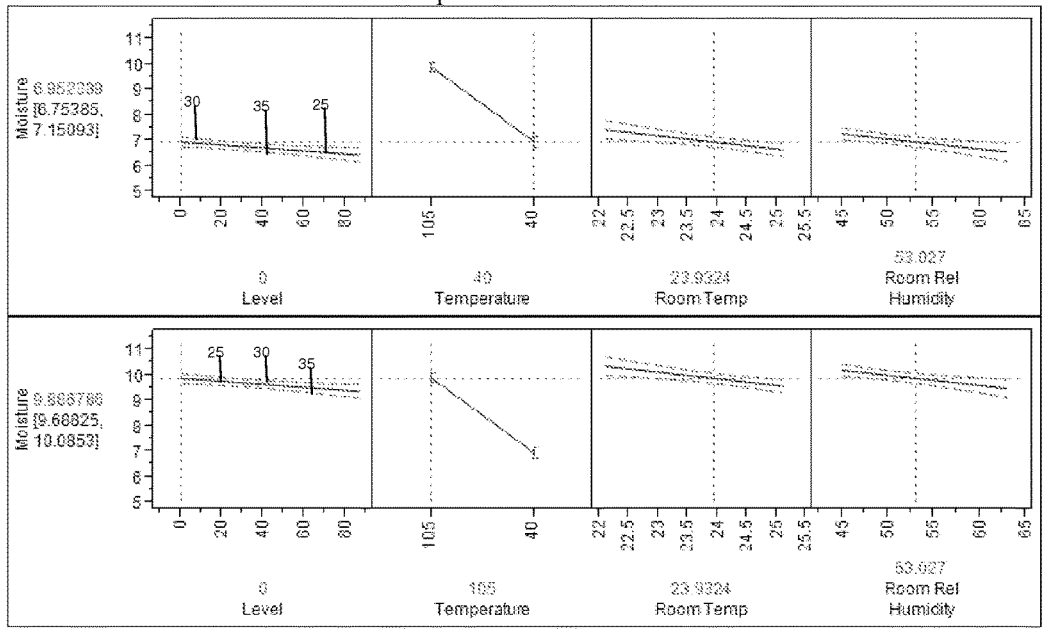

A method for increasing moisture retention in soils is provided. More specifically the present invention provides a method for identifying humectant compositions that effectively increase the moisture retention rate of soils when applied at effective amounts to the soil. Also provided are effective humectant compositions that result from the method for use on a particular soils or groups of soils.

The humectant composition is typically applied to a soil, often in solution form with a polar liquid component, to form a treated soil and functions to slow the rate of evaporation or loss of the polar liquid component from the solution after treating the soil with the solution. Even after evaporation or loss of the polar liquid component from the solution, the humectant composition may remain on the soil. As such, the humectant composition remaining on the soil can retain polar liquids that are subsequently applied onto the treated soil or already present on the soil prior to application of the humectant composition. The humectant composition is ideal for applications in which it would be desirable to slow evaporation or loss of polar liquids from soils, such as in the agricultural, botanical, and construction industries as described in further detail below.

The "polar liquid component" refers to any polar compound or combination of such compounds that is liquid at ambient temperature of about 21° C. and that is present in solution (save for distinct components referred to herein, such as the humectant composition, that are specifically defined as different from the polar liquid component). Thus, the polar liquid component may contain one or more polar liquid compounds including, but not limited to, water; alcohols such as methanol, ethanol, propanol, and butanol; acids such as acetic acid and formic acid; and combinations thereof. For most applications, the polar liquid component typically includes substantially only water. Stated differently, in this embodiment the polar liquid component typically only includes water, but impurities or other compounds that may fit the definition of a polar liquid compound but that are unintended for inclusion in the solution may also be present within the solution in trace amounts (i.e., in combined amounts of less than or equal to 1% by weight based upon the total weight of the polar liquid component). In addition to or as an alternative to water, the polar liquid component may include an antifreeze compound such as propylene glycol and/or ethylene glycol. It is to be appreciated that the instant invention is useful for any application in which retention of any polar liquid component is desired (with slowing of evaporation or loss of the polar liquid component desired) such that certain applications may benefit from a combination of polar liquid compounds present in the solution as the polar liquid component, or may benefit from the presence of polar liquids other than water.

For the purposes of the present invention, the term "polar liquid" or "polar liquid component" may alternatively be referred to as "moisture" as it relates to soils. Thus, for example, the term "moisture content" as it relates to soils refers to the polar liquid content or polar liquid component content of the soil. Similarly, the term "retaining moisture" as it relates to the soils refers to the ability of the soil to retain the polar liquid or polar liquid component. Stated yet another way, the term "moisture" is used interchangeably herein with the term "polar liquid."

The soil to be treated with the humectant composition refers to various types of soils for diverse purposes. For example, in one embodiment, the humectant composition may be applied to soils for purposes including, but not limited to, dust abatement, hydration, and inhibition of solidification of liquid and/or semi-solid compositions (e.g., through extended hydration). In all embodiments, the soil may be undisturbed immediately prior to application of the humectant composition onto the soil. More specifically, the soil may be disposed on the ground or in a found state immediately prior to application of the humectant composition.

As noted above, the present invention relates generally to a method for determining whether a particular humectant composition is an "effective humectant composition" for increasing moisture retention of a particular soil or group of similar soils over a range of applied humectant level concentrations. The method may then be expanded for use to determine whether a particular class of humectant compositions is suitable for use in one or a group of particular soils.

In general, the method of the present invention involves determining a particular soil to be evaluated for moisture content and testing a sample of the soil (i.e., soil sample) to determine its moisture content at some desired minimum humectant concentration value of interest. For the purposes of the description herein, the "desired minimum humectant concentration level of interest", as defined herein, may be zero (i.e., prior to the application of the humectant composition to the soil) or above zero (i.e., after application of a minimum amount of humectant composition to the soil), and is hereinafter referred to as the "minimum humectant concentration level."

The humectant composition is applied to the soil as a concentrate or more typically in solution form with a polar liquid component as defined above. The term "humectant concentration level" refers to the concentration of the humectant composition itself not including the polar liquid component.

The soil may then be contacted with an additional amount of the humectant composition (i.e., the humectant composition is applied or otherwise introduced onto the soil) above the minimum humectant concentration level (i.e., at a first humectant concentration level) and the treated soil is reevaluated for moisture content at the first humectant concentration level. Preferably, this evaluation is performed under the same test conditions as with the minimum humectant concentration level (i.e., at the same temperature and the same relative humidity). Alternatively, a separate soil sample may be contacted with the humectant concentration at the first humectant concentration level and evaluated for moisture content at the first humectant concentration level.

The soil sample may then be contacted with an additional amount of the humectant composition such that the total amount of humectant composition applied to the soil sample is at a desired maximum humectant concentration level of interest and the treated soil sample is reevaluated for moisture content at the maximum humectant concentration level. For the purposes of the description herein, the "desired maximum humectant concentration level of interest", as defined herein, is referred to as the "maximum humectant concentration level." Alternatively, a separate soil sample is contacted with the humectant concentration at the maximum humectant concentration level and evaluated for moisture content at the maximum humectant concentration level.

In certain embodiments, the maximum humectant concentration level for soils is 86.5 parts of the humectant composition per million parts of the soil. Stated another way, the treated soil includes a maximum of 86.5 parts of the humectant composition per million parts of the soil without treatment.

Optionally, the soil is also contacted with the humectant composition at one or more humectant concentration levels between the minimum and maximum humectant concentration level, and different than the first humectant concentration level, and the treated soil is evaluated for moisture content at each of these alternative humectant concentration levels (i.e., a second humectant concentration level).

The moisture content of the treated soil at each applied humectant concentration level is repeated one or more times (i.e., at least one additional time) on additional soil samples to generate an average moisture content for each applied humectant concentration level from the minimum humectant concentration level to the maximum humectant concentration level.

An average slope curve is then generated by averaging the measured moisture content of the treated soil at each applied humectant concentration level and plotting the averages onto a curve from the minimum humectant concentration level to the maximum humectant concentration level in a manner that factors in each applied humectant concentration level between the minimum humectant concentration level and the maximum humectant concentration level, preferably through the use of commercially available statistical software, such as JMP statistical software available from SAS Institute of Cary, N.C. In addition, a plot of an upper error limit slope curve and a lower error limit slope curve associated with the average slope curve at a p value of 0.05 are also plotted using the same or additional commercially available statistical software.

In statistics, the "p value" represents the population proportion of successes. The p value thus is the probability of obtaining a test statistic at least as extreme as the one that was actually observed. For the purposes of the present invention, a p value of 0.05 means that there is a 1 in 20 chance that the average test value obtained falls outside a calculated range of average moisture content values that are statistically significant. Stated differently, a p value of 0.05 means that there is a 95% confidence level that the average test value falls within a desired range of values. For the purposes of the present invention, the p value relates to the allowable variation in the average moisture content of the soil along the average slope curve line for the range of humectant concentration levels from the minimum humectant concentration level to the maximum humectant concentration level and still be statistically significant.

Figure 2:
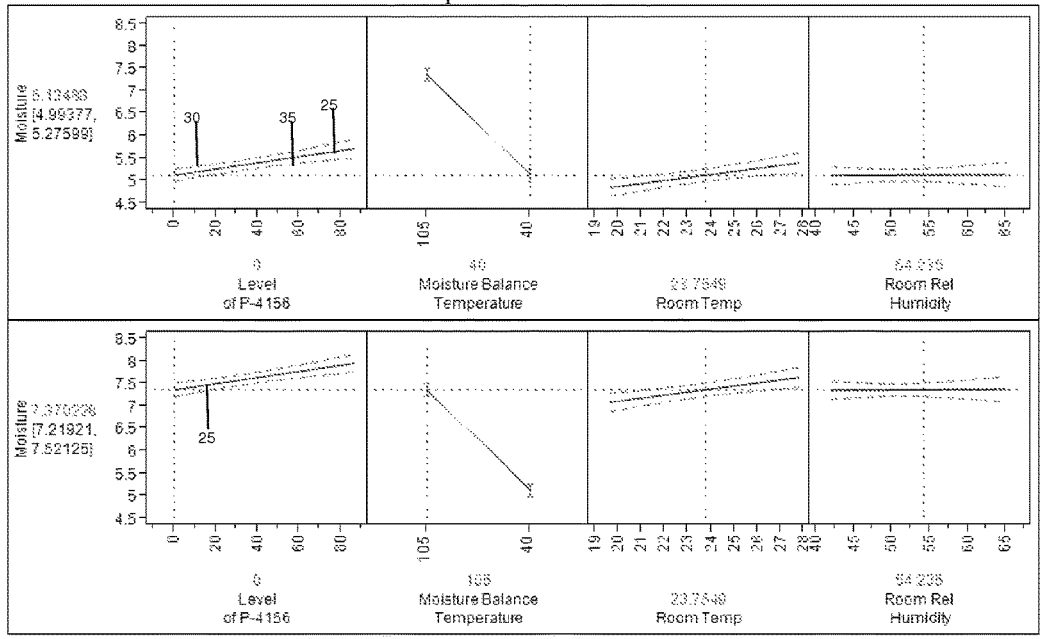
Figure 2:
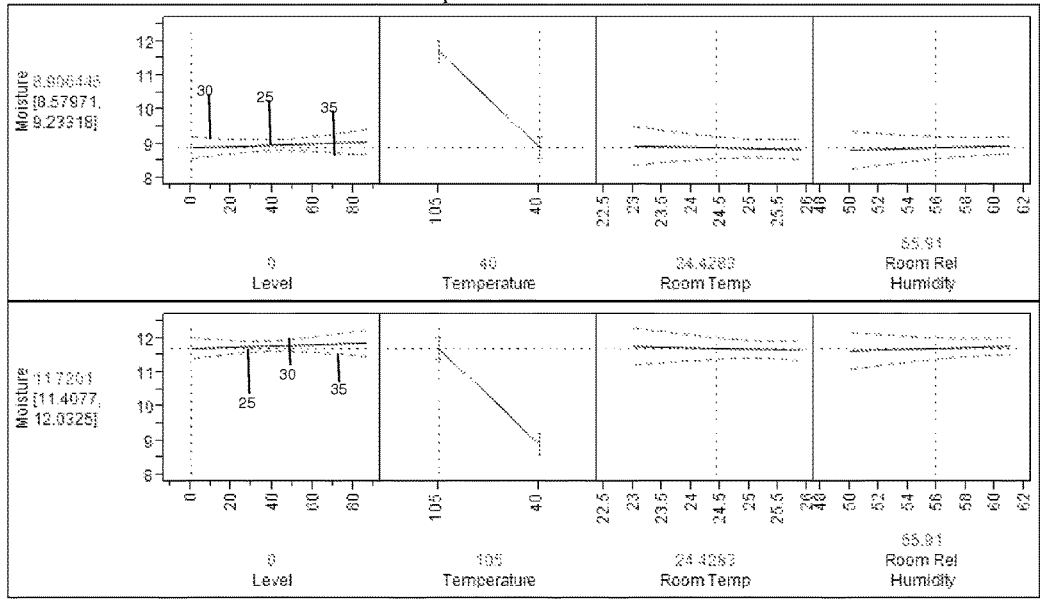
Figure 3:
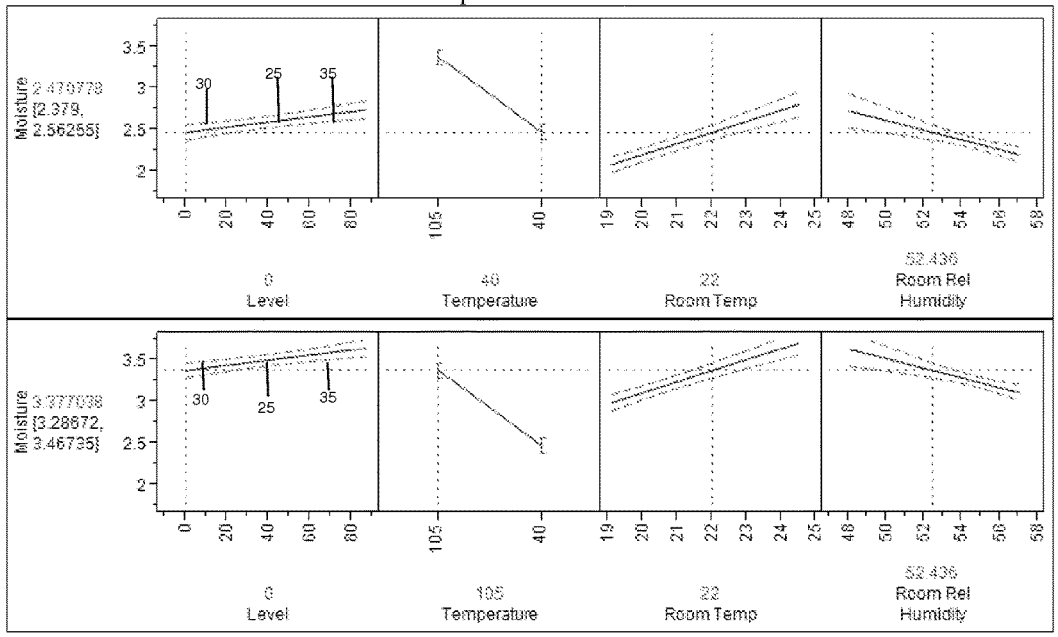
FIGS. 3 and 4 illustrate Fit Model Analysis graphs plotting moisture content for one humectant composition (Sample B) in four representative soil types utilizing two Mettler moisture balances in accordance with the method of the present invention.
Figure 3:
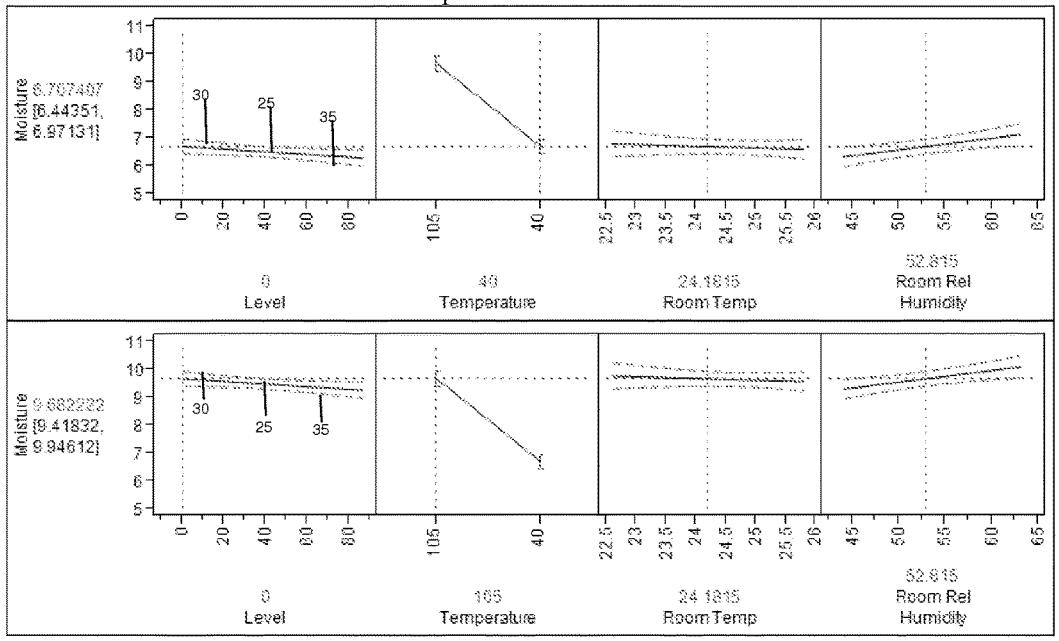
Figure 4:
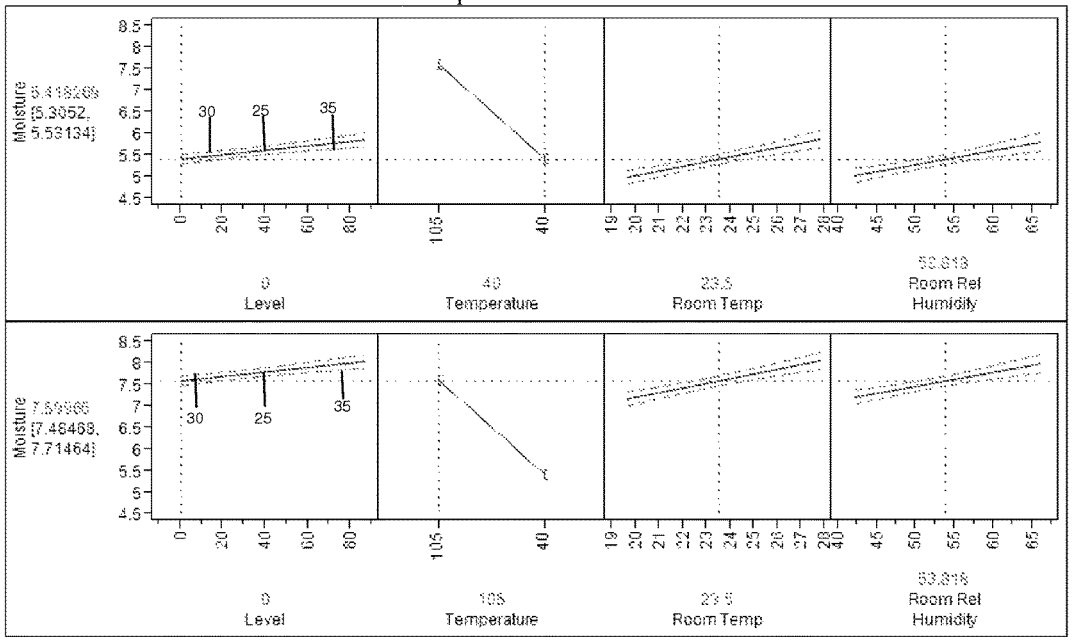
Figure 4:
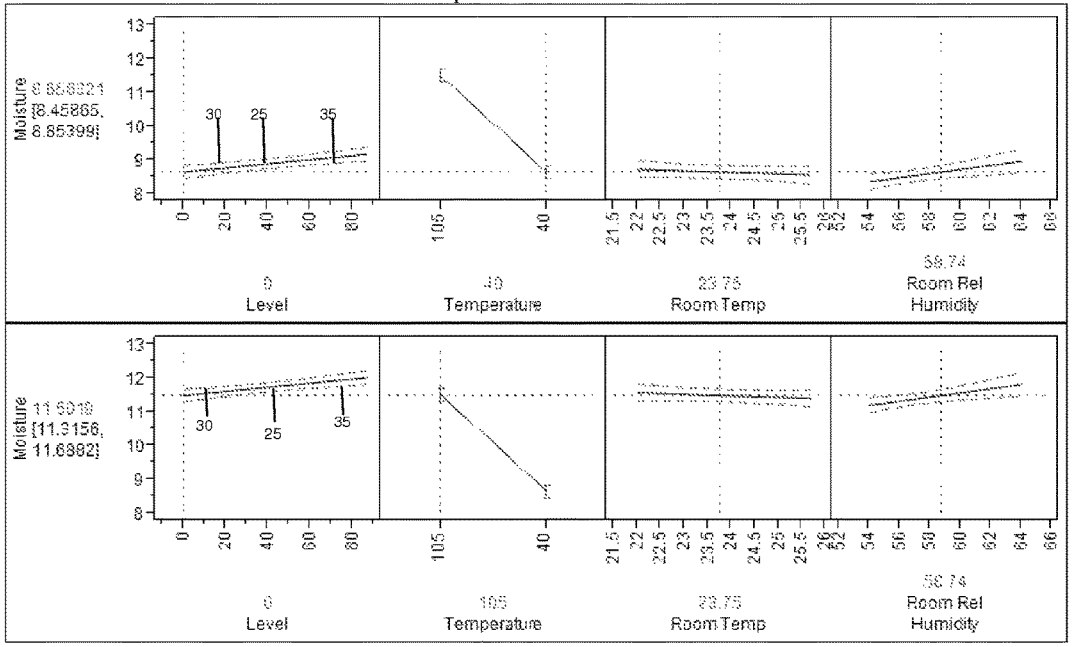
Figure 5:
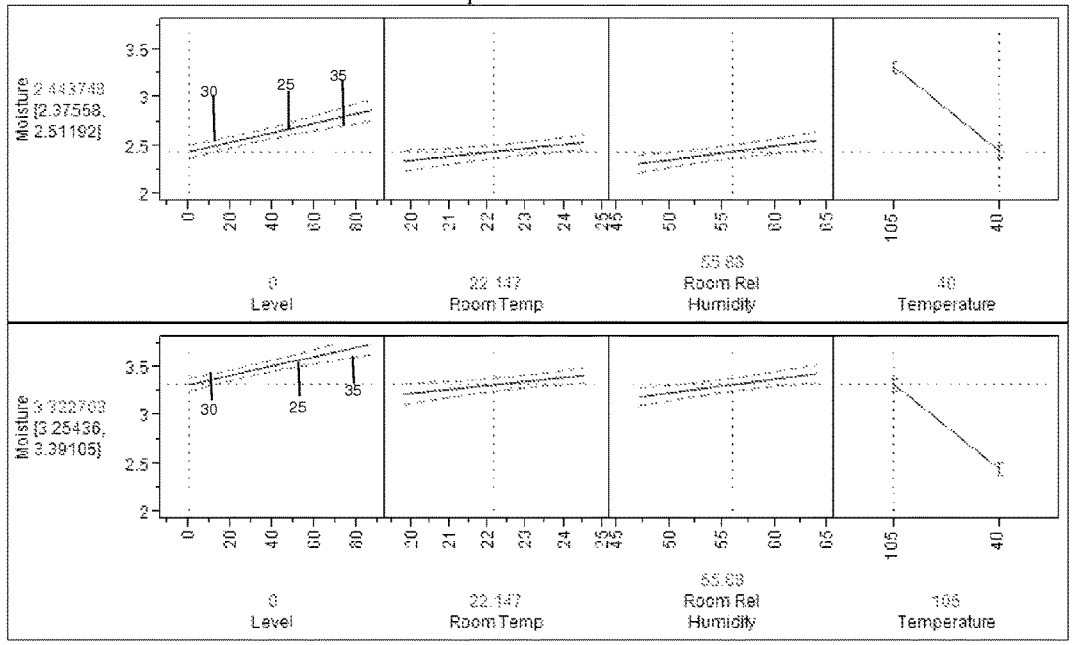
FIGS. 5 and 6 illustrate Fit Model Analysis graphs plotting moisture content for one humectant composition (Sample C) in four representative soil types utilizing two Mettler moisture balances in accordance with the method of the present invention.
Figure 5:
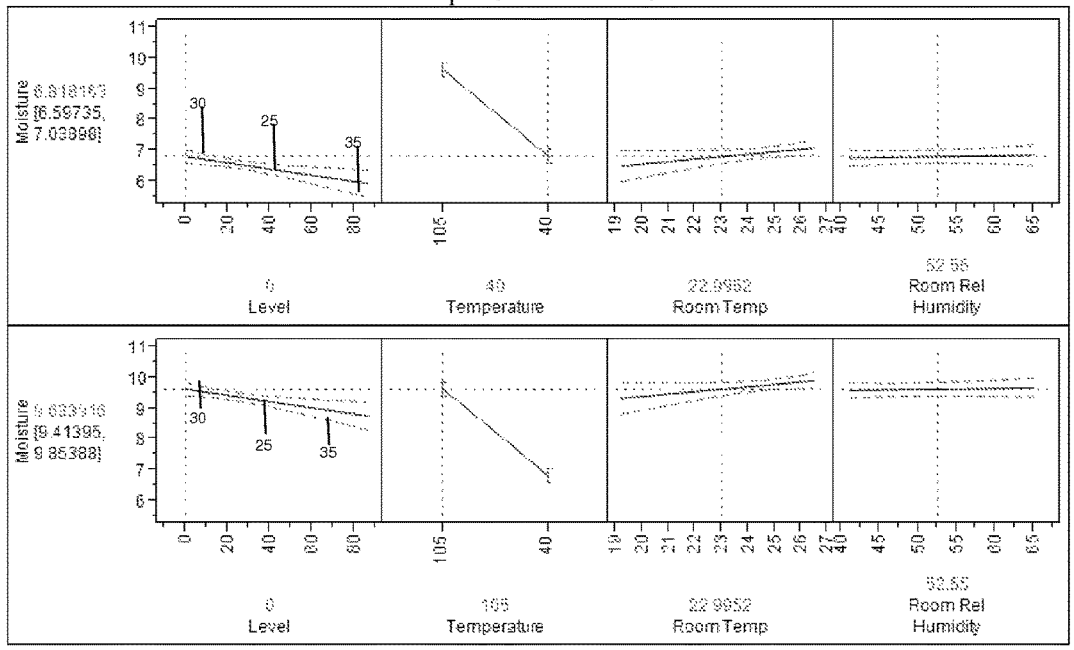
Figure 6:
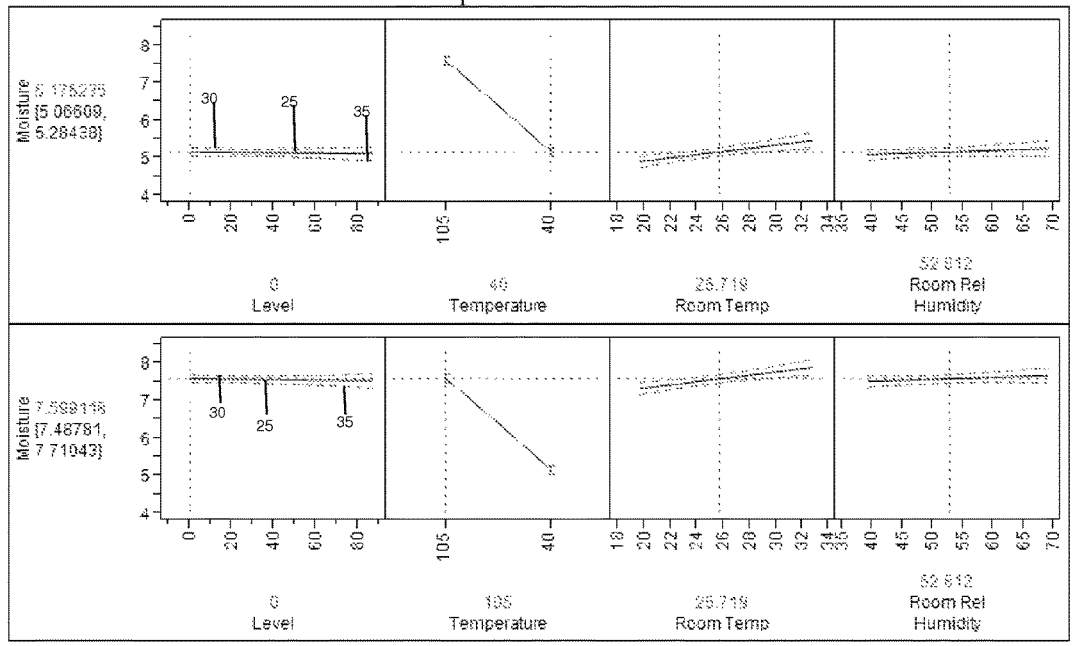
Figure 6:
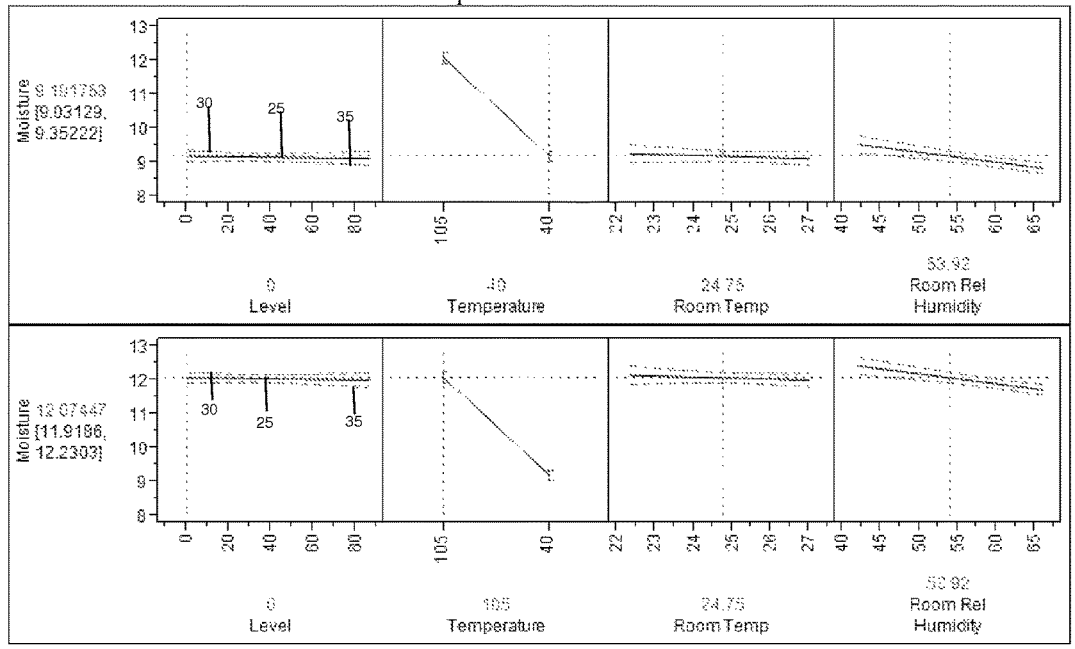
Figure 7:
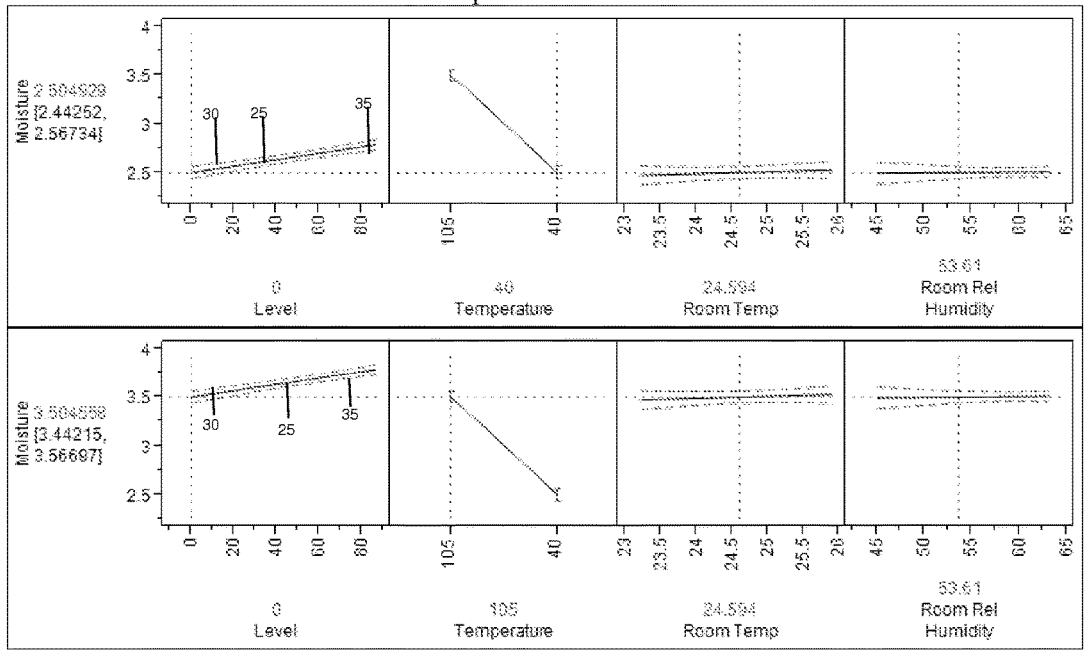
FIGS. 7 and 8 illustrate Fit Model Analysis graphs plotting moisture content for one humectant composition (Sample D) in four representative soil types utilizing two Mettler moisture balances in accordance with the method of the present invention.
Figure 7:
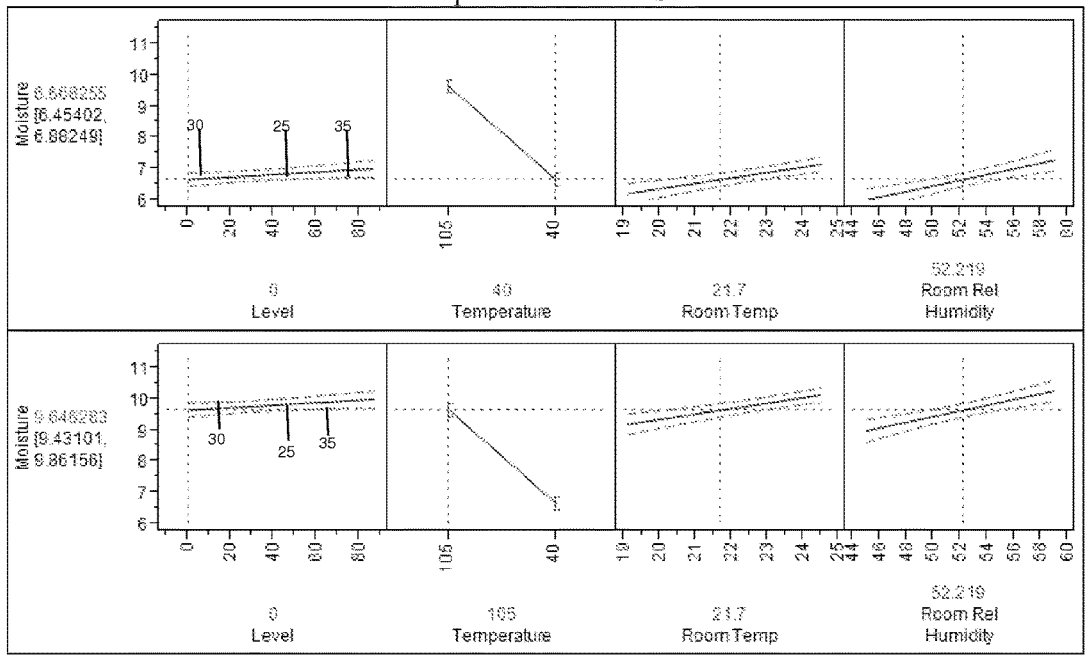
Figure 8:
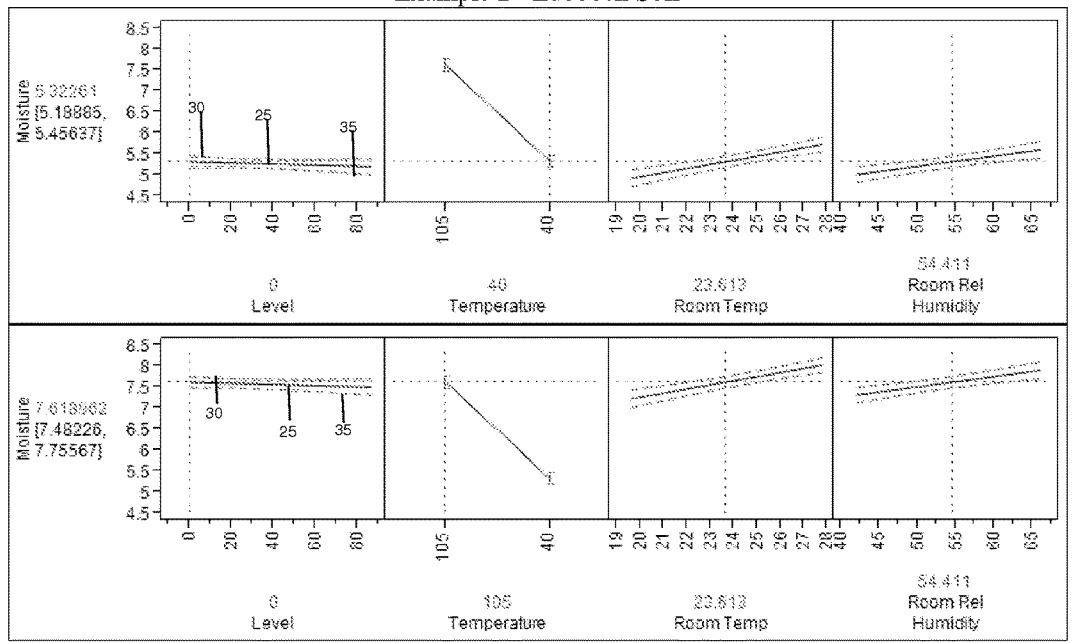
Figure 8:
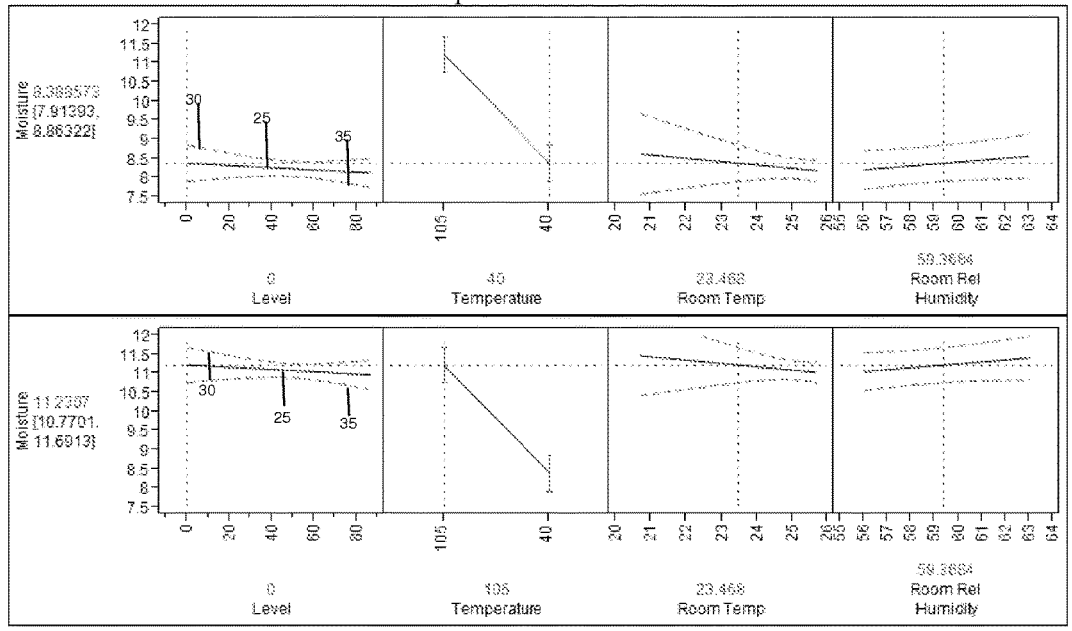
Figure 9:
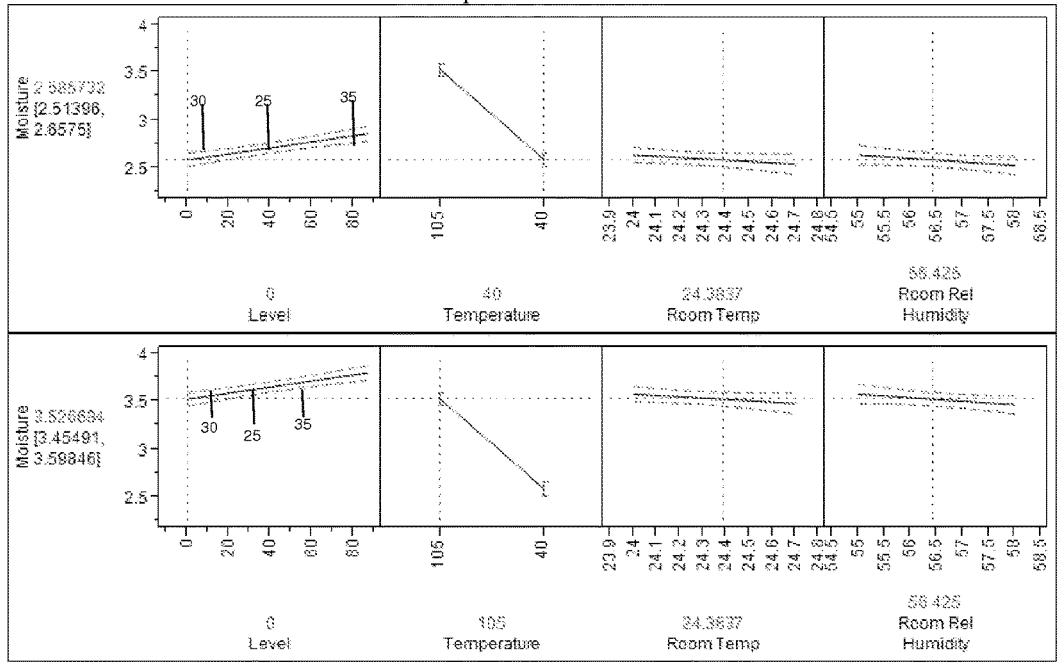
FIGS. 9 and 10 illustrate Fit Model Analysis graphs plotting moisture content for one humectant composition (Sample E) in four representative soil types utilizing two Mettler moisture balances in accordance with the method of the present invention.
Figure 9:
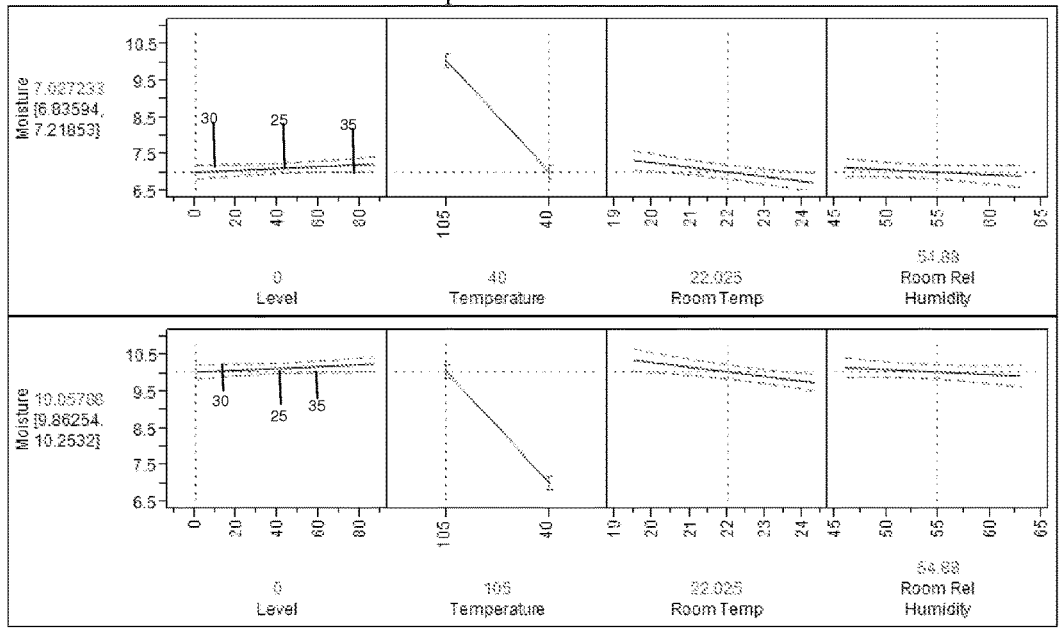
Figure 10:
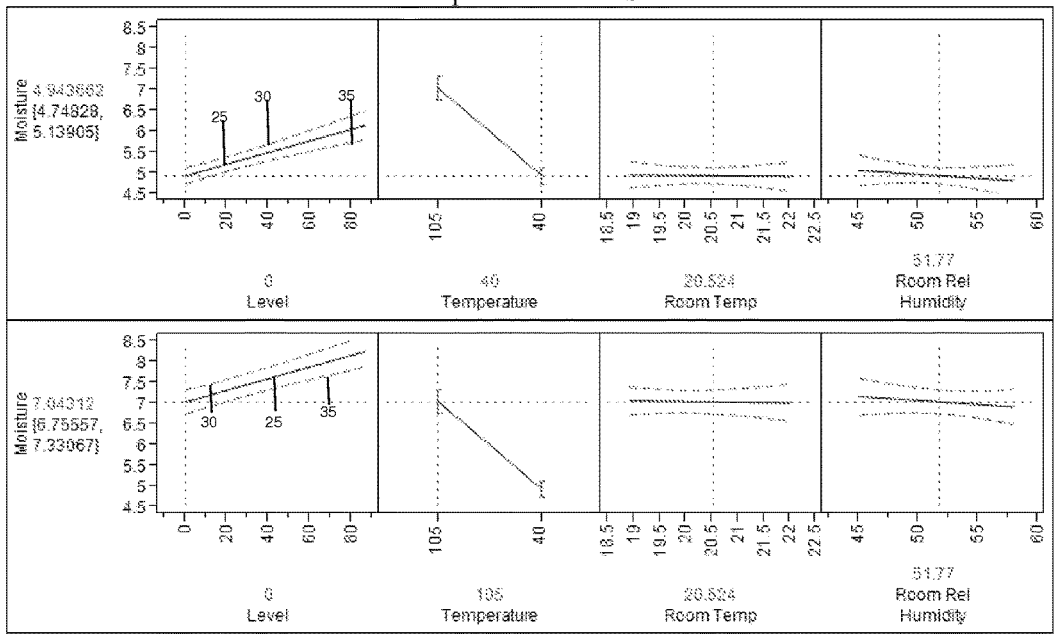
Figure 10:
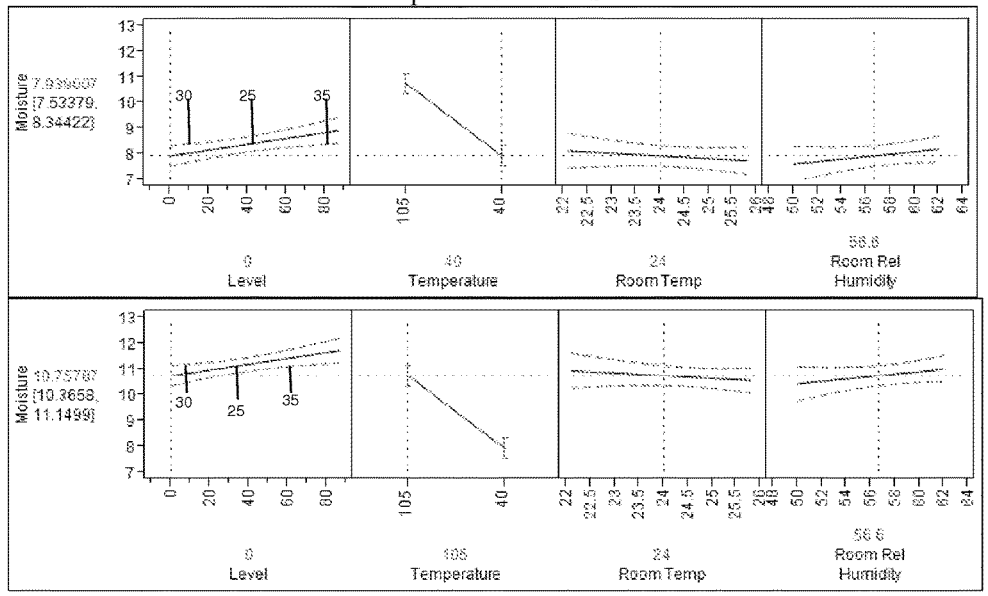
Figure 11:
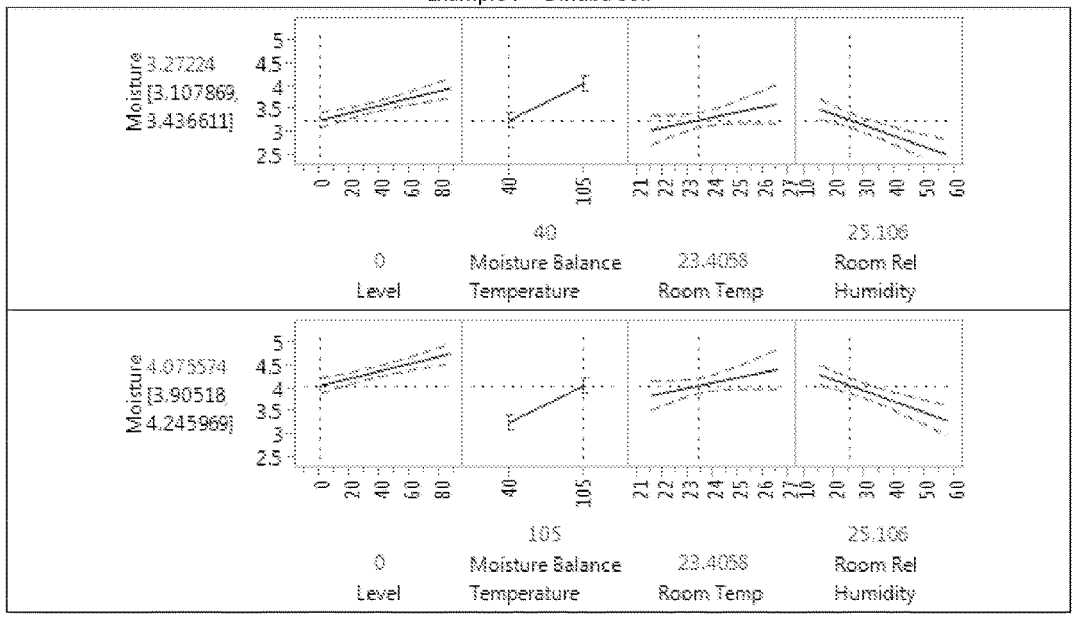
FIGS. 11 and 12 illustrate Fit Model Analysis graphs plotting moisture content for one humectant composition (Sample F) in four representative soil types utilizing two Mettler moisture balances in accordance with the method of the present invention.
Figure 11:
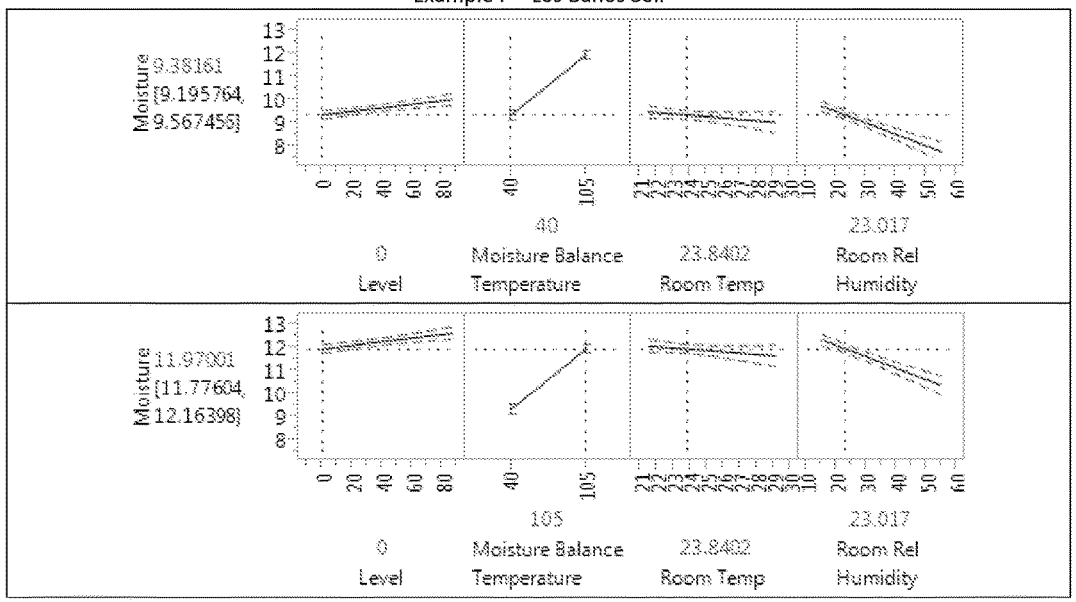
Figure 12:
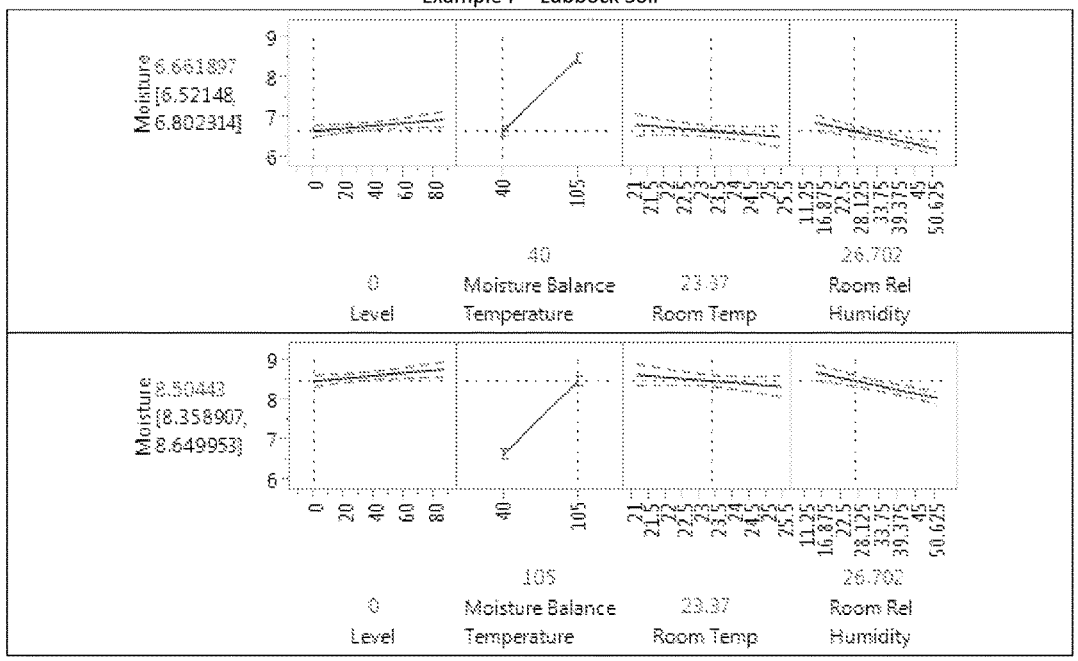
Figure 12:
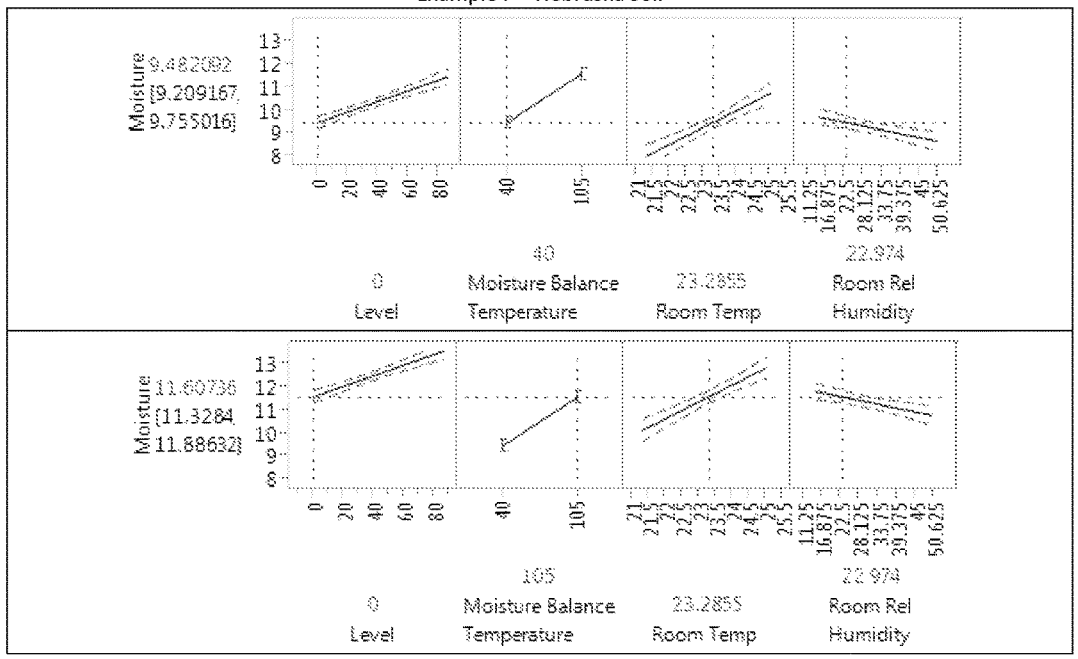
Figure 13:
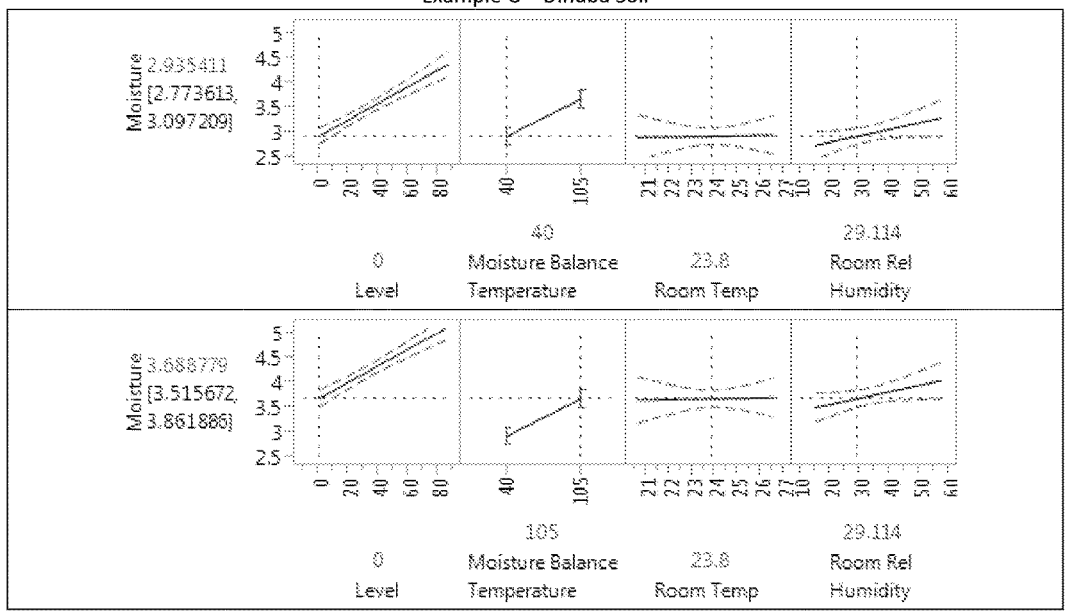
FIGS. 13 and 14 illustrate Fit Model Analysis graphs plotting moisture content for one humectant composition (Sample G) in four representative soil types utilizing two Mettler moisture balances in accordance with the method of the present invention.
Figure 13:
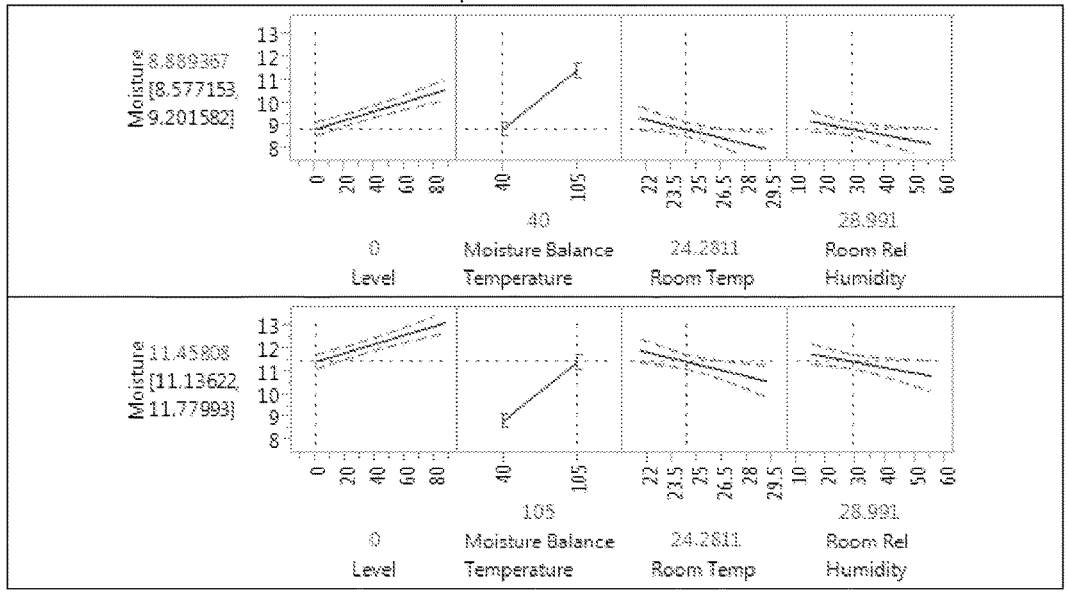
Figure 14:
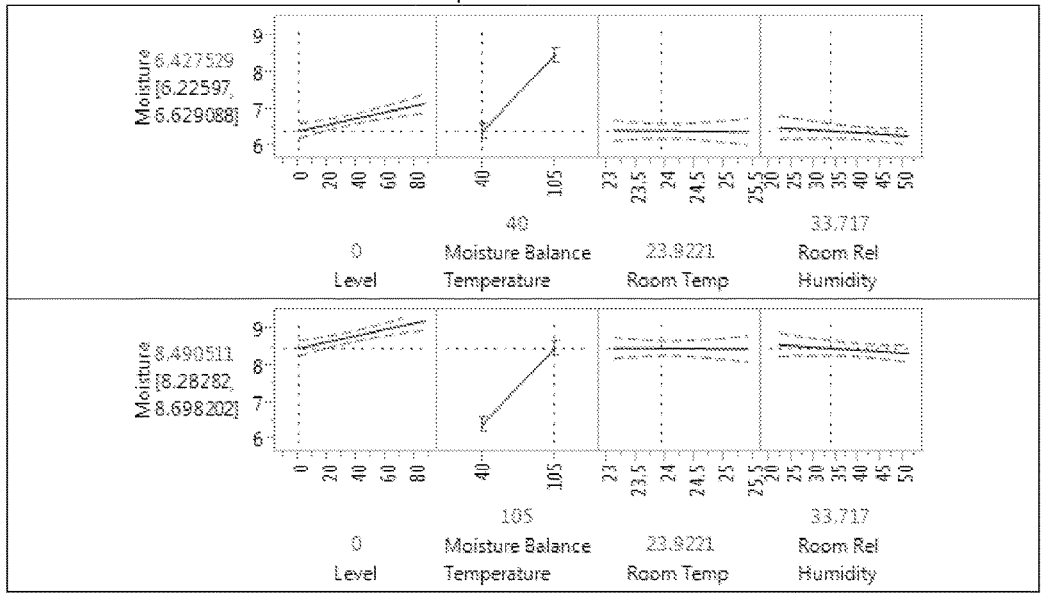
Figure 14:
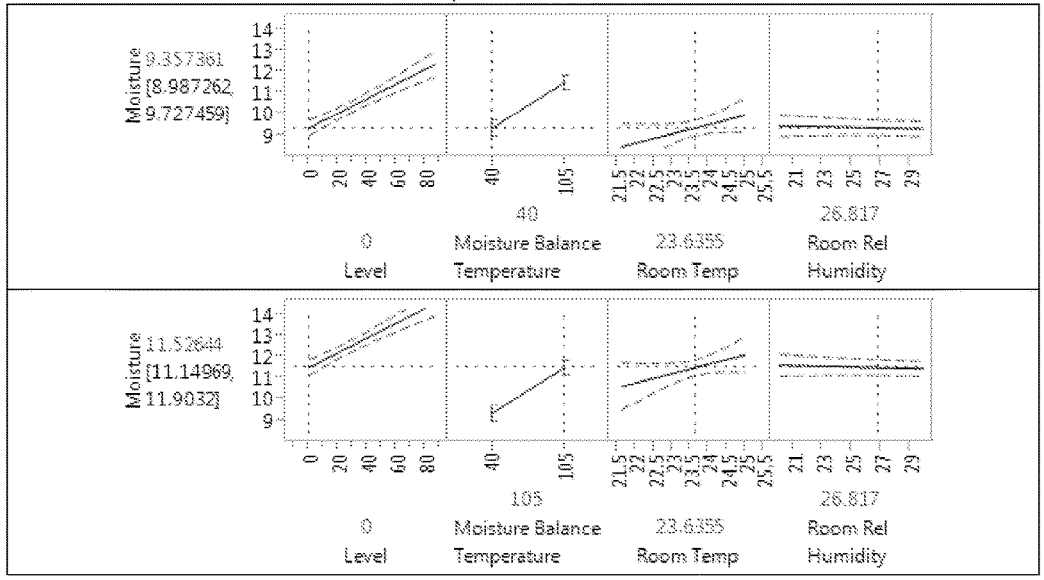
Figure 15:
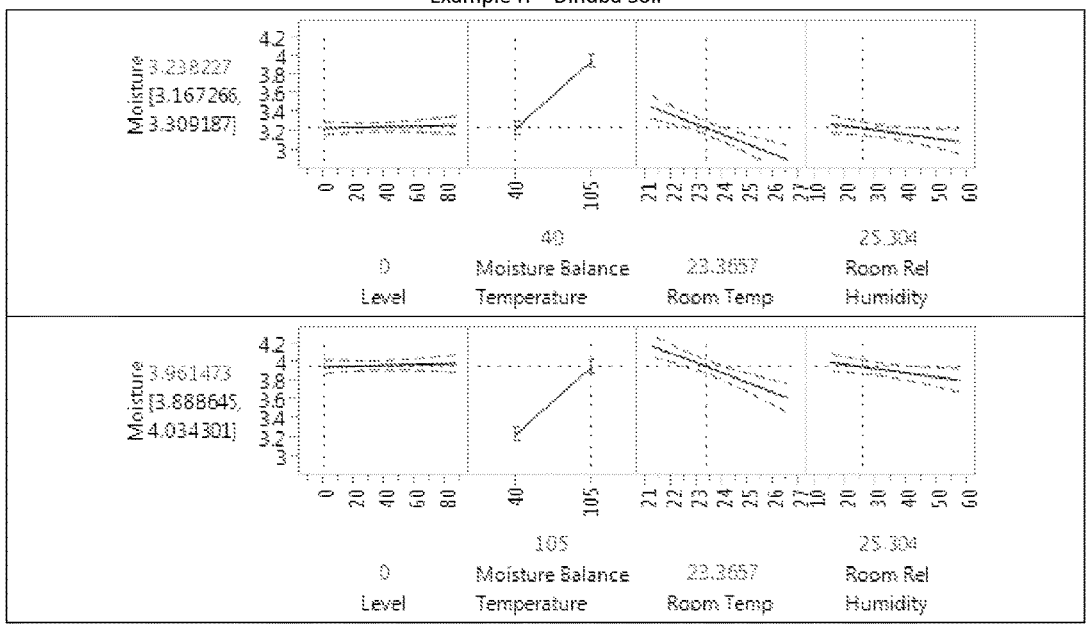
FIGS. 15 and 16 illustrate Fit Model Analysis graphs plotting moisture content for one humectant composition (Sample H) in four representative soil types utilizing two Mettler moisture balances in accordance with the method of the present invention.
Figure 15:
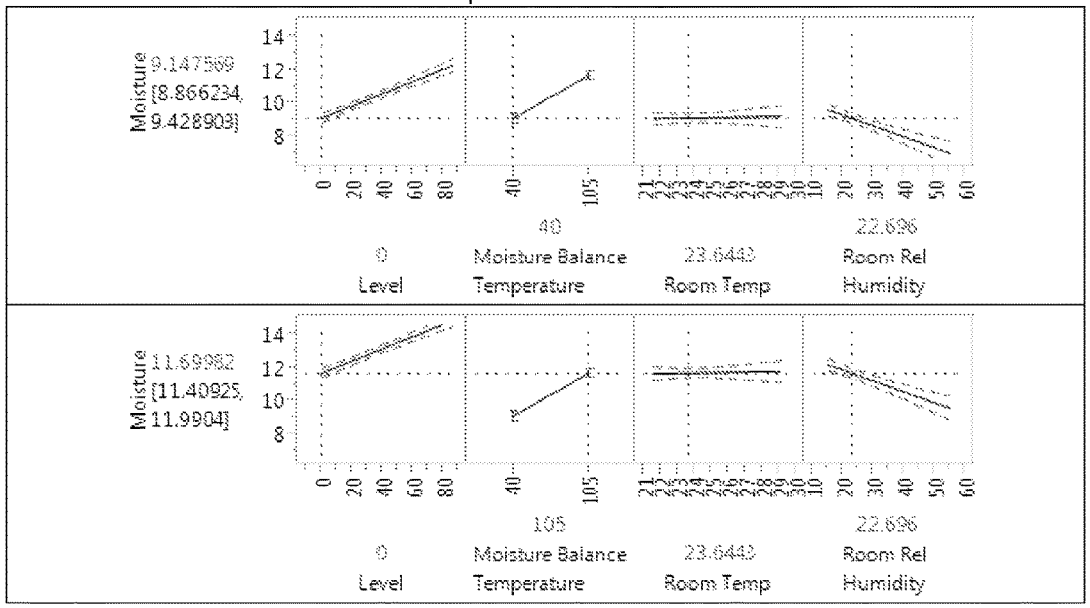
Figure 16:
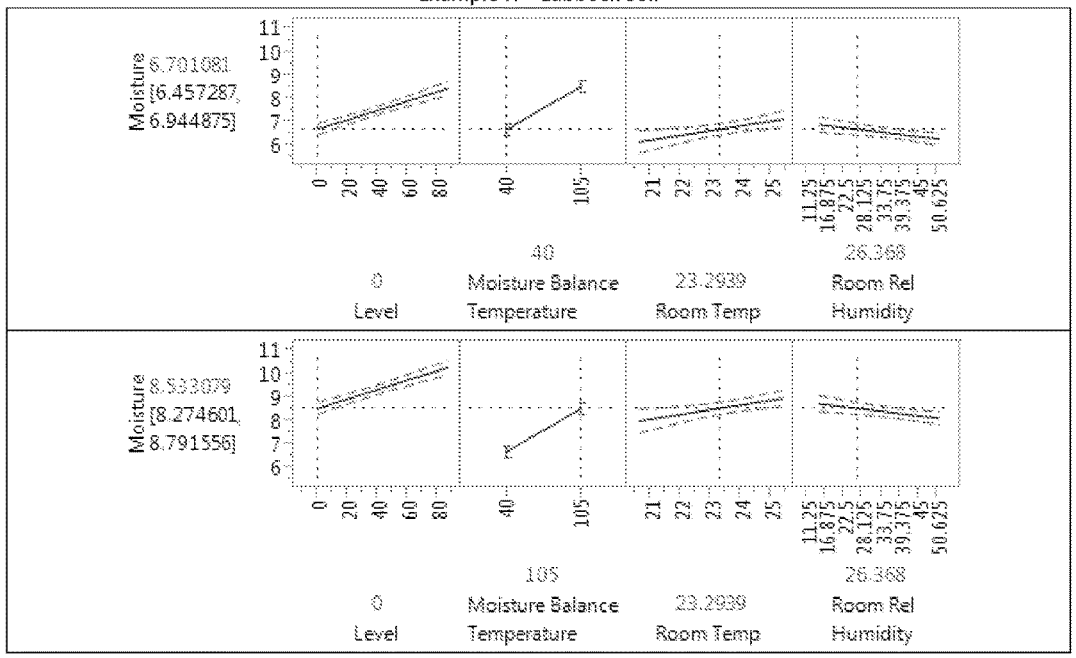
Figure 16:
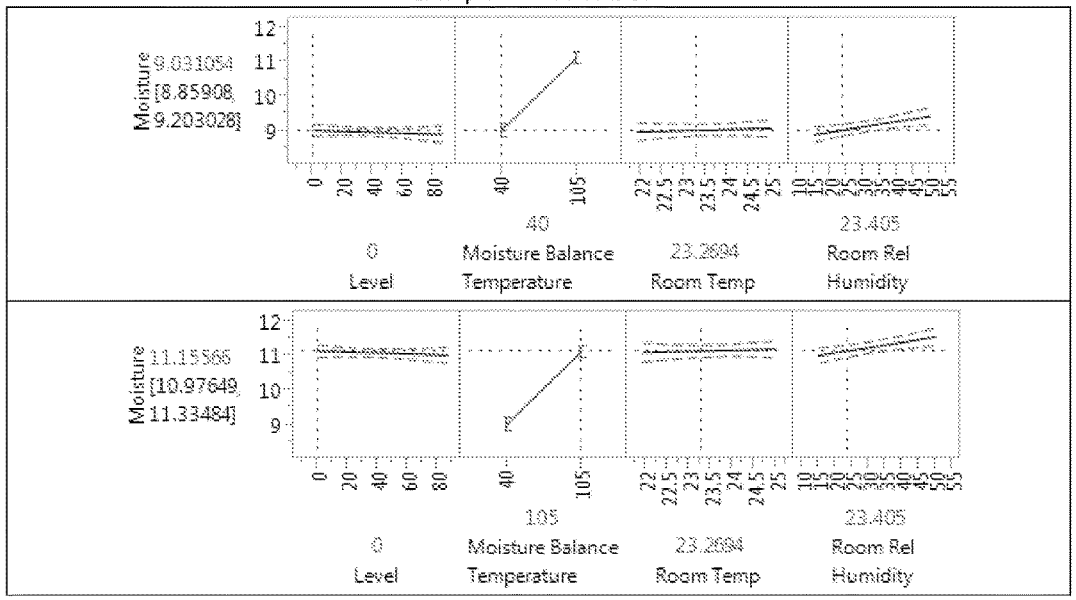
Figure 17:
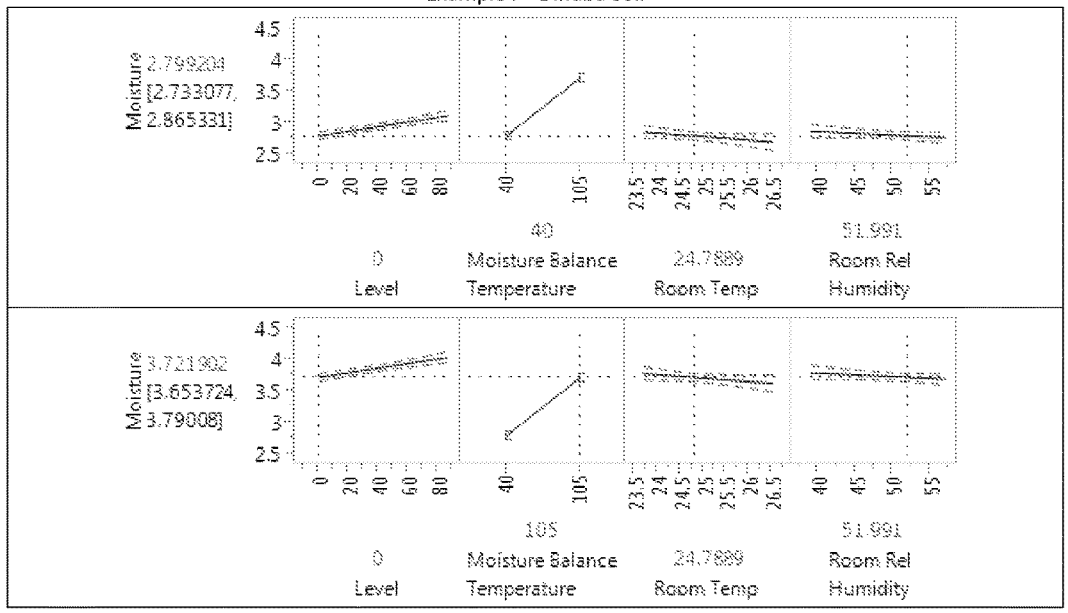
FIGS. 17 and 18 illustrate Fit Model Analysis graphs plotting moisture content for one humectant composition (Sample I) in four representative soil types utilizing two Mettler moisture balances in accordance with the method of the present invention.
Figure 17:
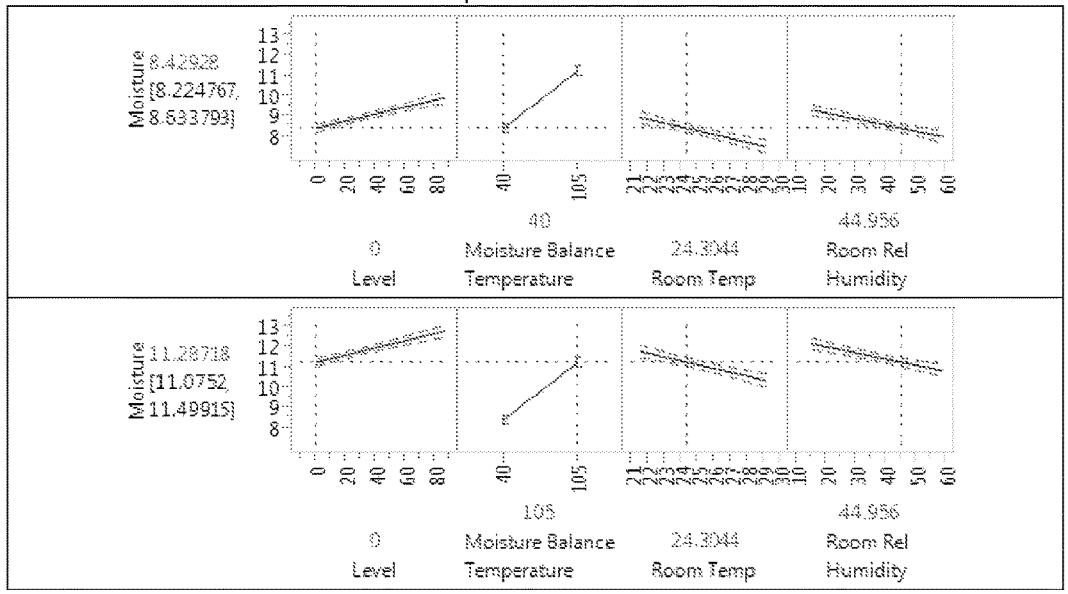
Figure 18:
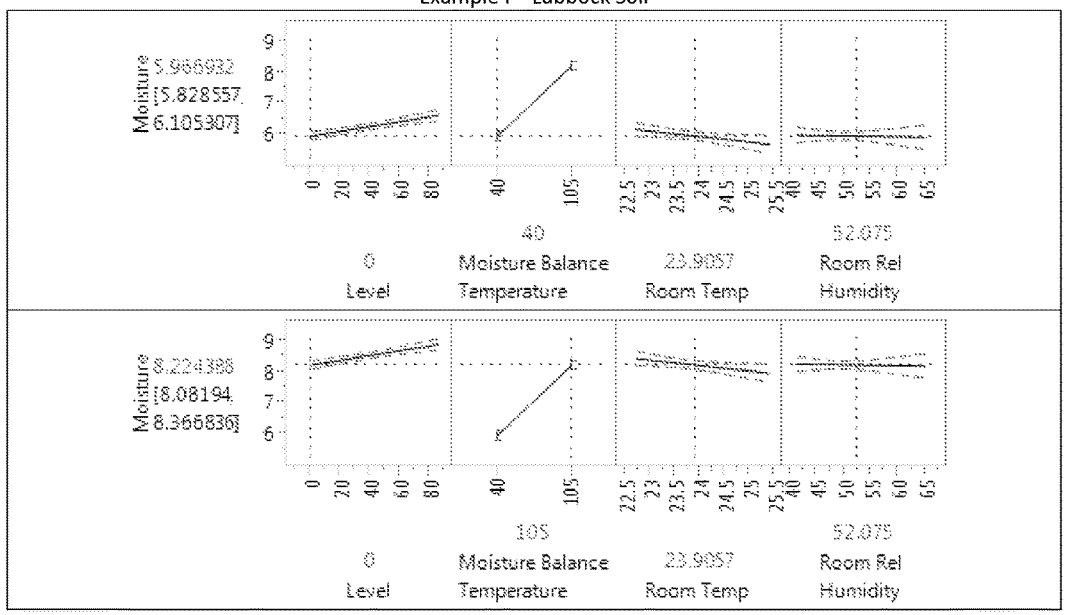
Figure 18:
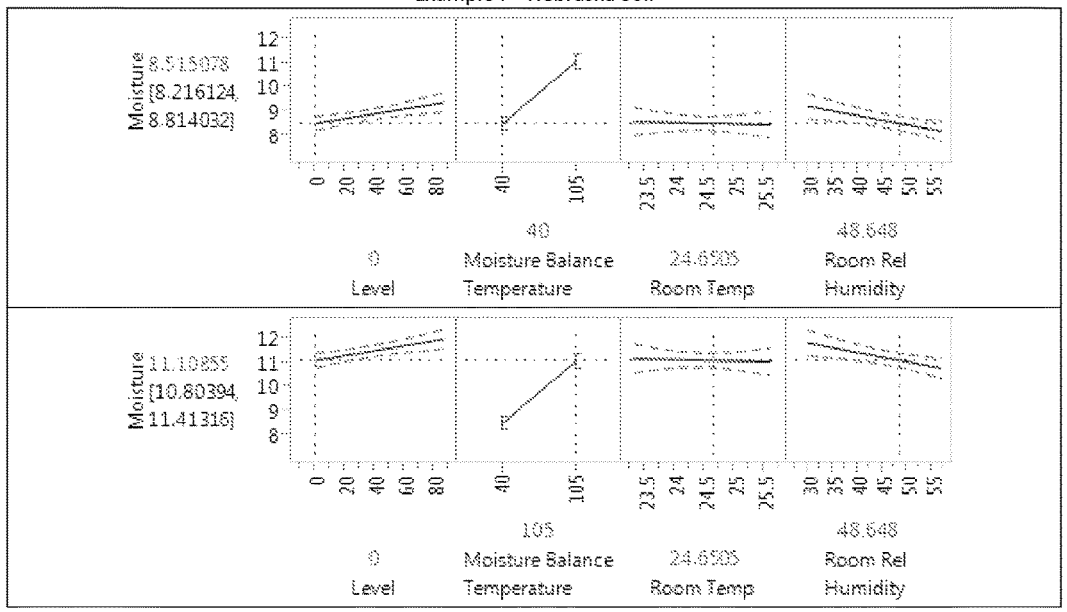
Figure 19:
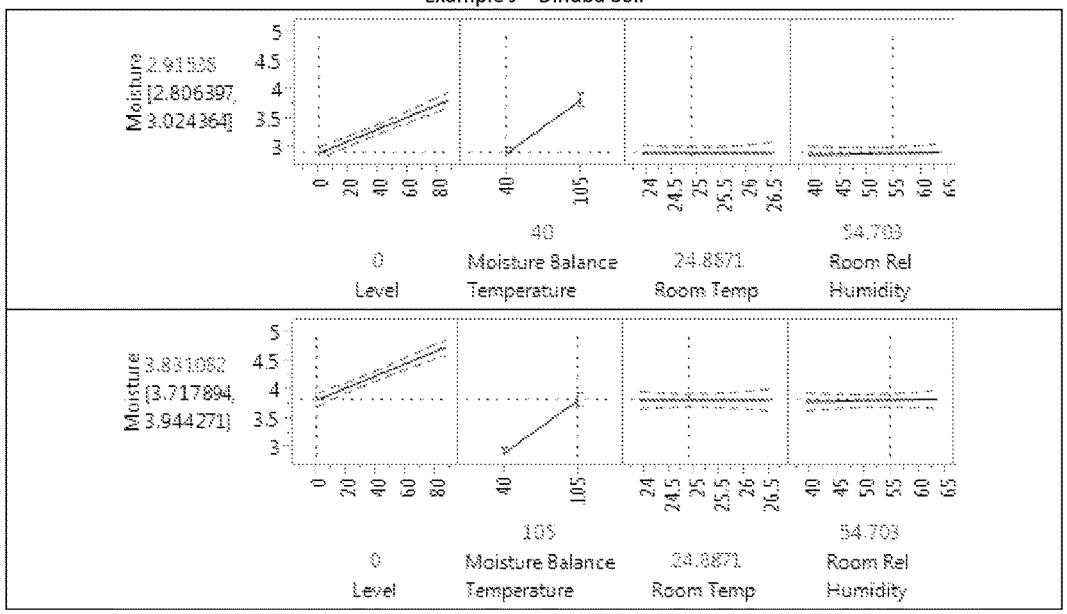
FIGS. 19 and 20 illustrate Fit Model Analysis graphs plotting moisture content for one humectant composition (Sample J) in four representative soil types utilizing two Mettler moisture balances in accordance with the method of the present invention.
Figure 19:
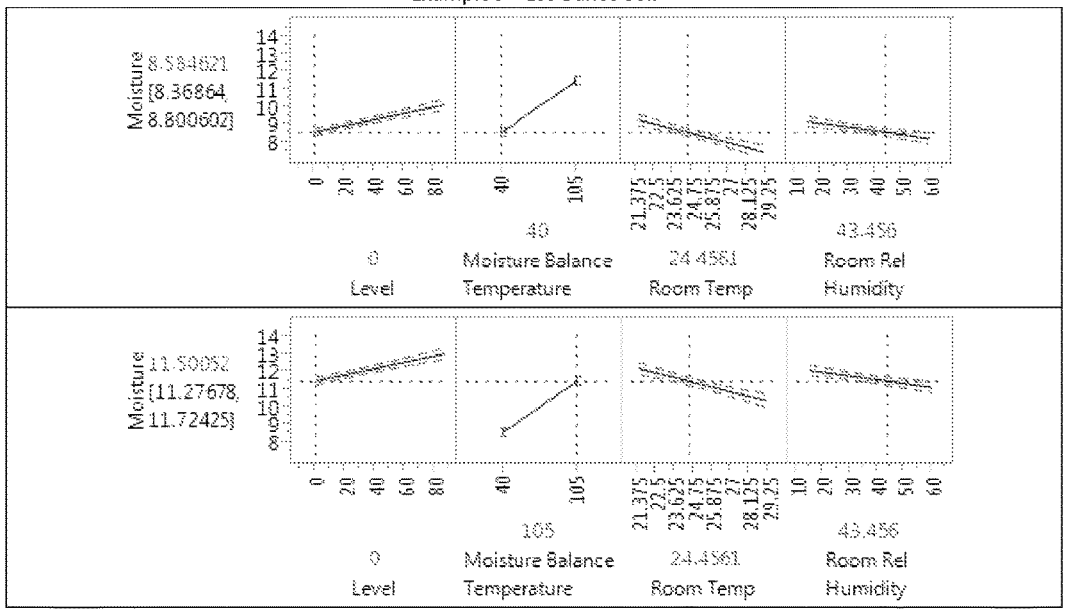
Figure 20:
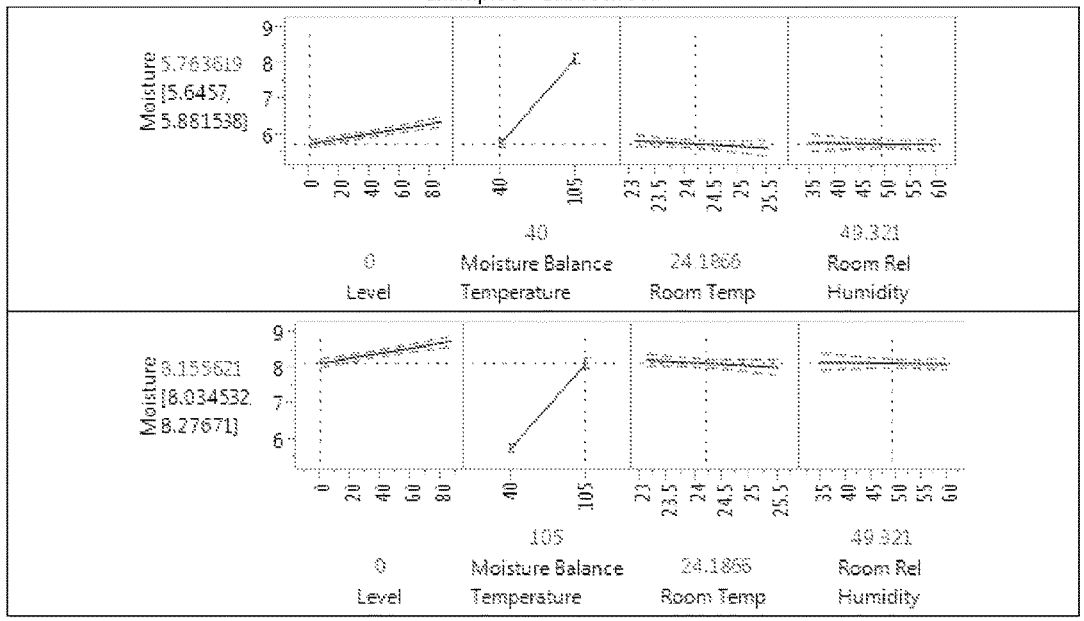
Figure 20:
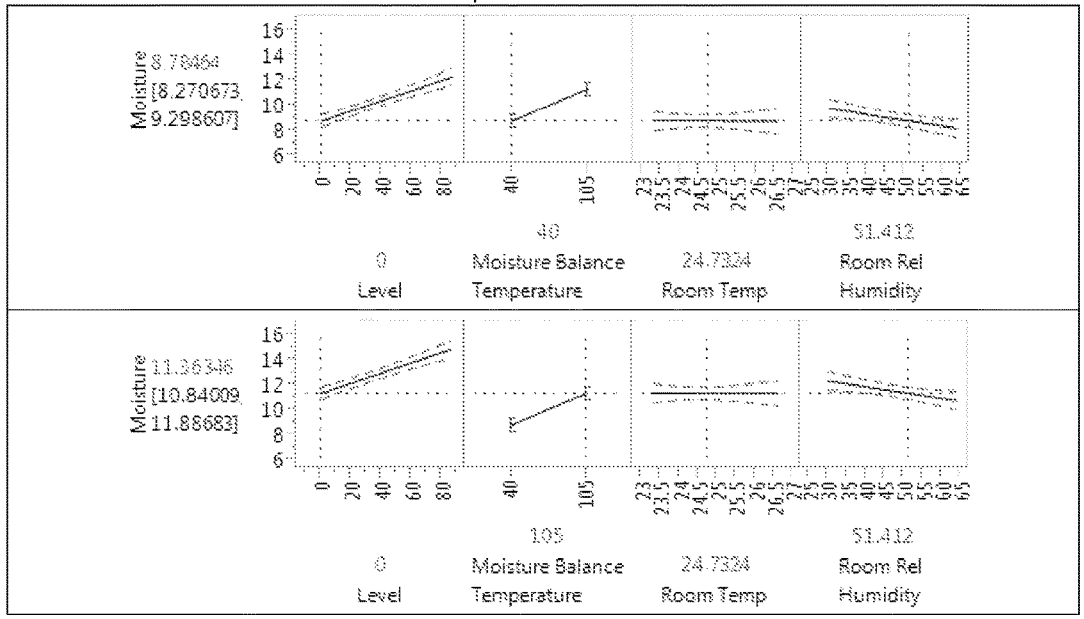

As will be illustrated in FIGS. 1-20 generated from the examples below, a p value of 0.05 or lower can be confirmed from the average slope curve (the average slope cure is shown as reference 25 in FIGS. 1-20) and its associated upper error line (the upper error line is shown as reference 30 in FIGS. 1-20) and lower error line (the lower error line is shown as reference 35 in FIGS. 1-20). If an imaginary horizontal line can be drawn that intersects the upper and lower error line 30, 35 along at least some portion of the average slope curve 25 between the minimum humectant concentration level and the maximum humectant concentration level, then the p value for the average slope curve 25 is 0.05 or less and therefore the average slope line generated is considered statistically significant to a 95% confidence level. If the imaginary line does not intersect both the upper and lower error lines 30, 35, then the generated average slope line 25 does not have a p value of 0.05 or less, and therefore the average slope line 25 generated is not considered statistically significant to a 95% confidence level.

If the average slope curve 25 is positive (i.e., wherein the average moisture content continuously increases along the entire length of the average slope curve 25 from the minimum humectant concentration level to the maximum humectant concentration level) and wherein the p value is determined to be 0.05 or less, then the humectant composition, for purposes of the present invention, is deemed to be an "effective humectant composition" for increasing moisture retention on the soil on which it is evaluated.

If either the average slope curve 25 is negative (i.e., wherein the average moisture content does not continuously increase along the entire length of the average slope curve 25 from the minimum humectant concentration level to the maximum humectant concentration level) or the determined p value is greater than 0.05, then the humectant composition, for purposes of the present invention, is deemed to be "not effective" or "ineffective" humectant composition for increasing moisture retention on the soil on which it is evaluated.

This analysis thus provides the framework for expanding the use to determine whether a particular humectant composition, or a particular class of humectant compositions, are effective (i.e., are "effective humectant compositions") for use on the particular soil evaluated. Once a humectant composition is determined to be an effective humectant composition for a particular soil, it may then be applied to the particular soil at concentration levels at or below the maximum humectant concentration level (i.e., at an effective amount) and provide the treated soil with increased moisture retention corresponding to the concentration level applied thereto.

The method in accordance with the present invention has been utilized to identify a range of compositions that have been found to be effective humectant compositions in increasing moisture retention in a wide variety of soils. More specifically, in certain embodiments, the compositions developed by the above method have been found to be effective humectant compositions for increasing the moisture retention rates in most known soil types as represented by four distinct representative soil types found in various locations in the United States. These representative soils include Dinuba soil, Los Banos soil, Lubbock soil, and Nebraska soil, whose compositions and characteristics are provided in Table 1 below. It is generally considered that if a humectant composition is an "effective humectant composition" in at least three of these representative soil types, the humectant composition will provide increased moisture retention rates, and hence be an effective humectant composition, on most soils found throughout the United States and the world. As used hereinafter, the term "effective humectant composition" refers to a humectant composition that is effective on at least three of the representative soils as determined by the method provided herein. The composition of these four representative soil samples in provided in Table 1 below:

Z represents a heteric copolymer derived from the alkoxylation reaction product of ethylene oxide and propylene oxide,
the subscript a is zero or a positive number,
the subscript b is zero or a positive number,
the subscript c is zero or a positive number,
the subscript a is a positive number when the subscript b is zero,
the subscript b is a positive number when the subscript a is zero, and
the subscript x is one or higher.

In certain related embodiments, the heteric copolymer Z is derived from the alkoxylation reaction product of ethylene oxide and propylene oxide and butylene oxide. In still other related embodiments, the heteric copolymer Z is derived from the alkoxylation reaction product of ethylene oxide and propylene oxide and styrene oxide. Still further, in other embodiments, the heteric copolymer Z is derived from the alkoxylation reaction product of ethylene oxide and propylene oxide and butylene oxide and styrene oxide.

In certain embodiments, $(CH_2CH(CH_3)O)_c$ comprises, at most, 10% by weight of the total weight of the composition.

In certain embodiments, an effective humectant composition identified by the above method comprises a polyol composition according to the formula:

$$Y[Z_a(CH_2CH_2O)_b(CH_2CH(CH_3)O)_c(CH_2CH(Ph)O)_dH]_x,$$

wherein
Ph is a phenyl group;
Y is derived from an organic compound having x reactive hydroxyl groups;
Z represents a heteric copolymer derived from the alkoxylation reaction product of ethylene oxide and propylene oxide,

TABLE 1

| Sample ID | OM % | Phosphorus | | | K ppm | Mg ppm | Ca ppm | Na ppm | pH | CEC meq/100 |
| --- | --- | --- | --- | --- | --- | --- | --- | --- | --- | --- |
| | | P1 ppm | P2 ppm | Bic ppm | | | | | | |
| Dinuba, CA | 0.8 | 73 | 104 | | 230 | 99 | 1429 | | 6.7 | 8.6 |
| Los Banos, CA | 1.4 | 42 | 113 | | 355 | 662 | 3406 | 388 | 7.3 | 25.1 |
| Lubbock, TX | 0.9 | 15 | 41 | | 435 | 612 | 1005 | | 7.3 | 11.2 |
| Nebraska | 3 | 115 | | | 690 | 272 | 1768 | | 5.1 | 20.8 |
| Dinuba Original (field 3A) | 0.75 | | | | 162 | 151 | 1610 | 28 | 6.6 | 10.5 |

| Sample ID | Percent Base Saturation | | | | | S | Sand % | Silt % | Clay % | Soil Type |
| --- | --- | --- | --- | --- | --- | --- | --- | --- | --- | --- |
| | K | Mg | Ca | H | Na | | | | | |
| Dinuba, CA | 6.9 | 9.6 | 83.5 | | | 84 | 57 | 23 | 20 | sandy clay loam |
| Los Banos, CA | 3.6 | 22 | 67.7 | | 6.7 | 868 | 20 | 43 | 37 | silty clay loam |
| Lubbock, TX | 10 | 45.5 | 44.5 | | | 23 | 76 | 12 | 12 | sandy loam |
| Nebraska | 8.5 | 10.9 | 42.5 | | | 24 | 14 | 60 | 26 | siloam |
| Dinuba Original (field 3A) | | | | | | | 59 | 29.3 | 11.7 | sandy loam |

In certain embodiments, an effective humectant composition identified by the above method comprises a composition according to the formula:

$$Y[Z_a(CH_2CH_2O)_b(CH_2CH(CH_3)O)_cH]_x,$$

wherein
Y is derived from an organic compound having x reactive hydroxyl groups;

the subscript a is zero or a positive number,
the subscript b is zero or a positive number,
the subscript c is zero or a positive number,
the subscript d is a positive number,
the subscript a is a positive number when the subscript b is zero,
the subscript b is a positive number when the subscript a is zero, and
the subscript x is one or higher.

In certain related embodiments, the heteric copolymer Z is derived from the alkoxylation reaction product of ethylene oxide and propylene oxide and butylene oxide. In still other related embodiments, the heteric copolymer Z is derived from the alkoxylation reaction product of ethylene oxide and propylene oxide and styrene oxide. Still further, in other embodiments, the heteric copolymer Z is derived from the alkoxylation reaction product of ethylene oxide and propylene oxide and butylene oxide and styrene oxide.

In certain embodiments, $(CH_2CH(Ph)O)_d$ comprises, at most, 10% by weight of the total weight of the composition, wherein Ph represents a phenyl group.

In certain embodiments, the weight average molecular weight ($M_w$) of the composition according to any of the embodiments described above ranges from 2000 to 6000 g/mol, such as from 2700 to 3300 g/mol, such as 3000 g/mol.

In certain embodiments, Y may be derived from a monofunctional alcohol (i.e., an organic compound having one reactive hydroxyl group), a difunctional alcohol (i.e., an organic reactive alcohol having two reactive hydroxyl groups), or a higher functional alcohol (i.e., an organic reactive alcohol having three or more reactive hydroxyl groups). In certain embodiments, Y is derived from a saturated alcohol, but in certain other embodiments may be derived from an unsaturated alcohol or derived from a combination of saturated and unsaturated alcohols.

In certain embodiments, Y is derived from a mixture of at least two organic alcohols having a different number of reactive functional hydroxyl groups.

Representative monofunctional alcohols include simple primary alcohols having the general formula $RCH_2OH$, secondary alcohols having the general formula $RR'CHOH$, or tertiary alcohols having the general formula $RR'R''COH$, where R, R', and R'' stand for alkyl groups.

Still other representative monofunctional alcohols include aryl alkanols or diaryl alkanols having single reactive hydroxyl groups such as naphthol.

Representative simple difunctional alcohols, or diols include simple chemical compounds containing two hydroxyl groups such as, for example, ethylene glycol; 1,4 butanediol; propylene 1,3 diol; and the like.

Representative simple higher functional alcohols, such as triols, tetraols and higher functional alcohols, include glycerol, pentaerythritol, and the like.

One exemplary, non-limiting humectant composition identified for use on the representative soils and formed in accordance with the above method is a first polyol composition that comprises the reaction product of: (i) 3% by weight of a trifunctional alcohol (i.e., an organic reactive alcohol having three reactive hydroxyl groups), (ii) 10 to 15% by weight of ethylene oxide, and (iii) 82 to 87% by weight of propylene oxide. In certain embodiments, the trifunctional alcohol is glycerol. In these embodiments, this first polyol composition is capped with at most 10% by weight of propylene oxide. In certain embodiments, this first polyol composition has a weight average molecular weight ($M_w$) ranging from 2000 to 6000 g/mol, such as from 2700 to 3300 g/mol, such as 3000 g/mol.

In still other embodiments, a second composition may be used in conjunction with the first polyol composition, wherein the second composition comprises the reaction product of: (i) 3% to 8% by weight of a monofunctional alcohol or a difunctional alcohol, (ii) 82 to 97% by weight of ethylene oxide, and (iii) 0 to 10% by weight of propylene oxide. The weight average molecular weight of the second composition ranges from 2000 to 6000 g/mol.

Another exemplary, non-limiting humectant composition identified for use on the representative soils and formed in accordance with the above method is a polyol composition comprises the reaction product of: (1) 2.5 to 3.1% by weight of a trifunctional alcohol, (ii) 50 to 80% by weight of ethylene oxide, and (iii) 16.9 to 47.5% by weight of propylene oxide. In certain embodiments, the trifunctional alcohol is glycerol. In certain embodiments, this additional polyol composition has a weight average molecular weight ($M_w$) ranging from 2000 to 6000 g/mol, such as 3600 g/mol.

In still further embodiments, the effective humectant composition comprises a graft polyol dispersion, in which 5 to 25% by weight of polyacrylic acid homopolymer is dispersed in a polyol composition formed in accordance with the present invention as described above. In certain of these embodiments, the graft polyol dispersion is formed by reacting acrylic acid, a macromer and a reaction moderator in the presence of a free radical polymerization initiator, the polyol composition, and heat.

The present invention thus provides a statistically sound and repeatable method for identifying whether a humectant composition is effective at increasing moisture retention for a particular soil or closely related group of soils. In certain embodiments, the method identifies effective humectant compositions for increasing moisture retention in at least three of the representative soils as described above, and thus is believed to be an effective humectant composition for increasing moisture retention over most, if not all, known soil types in the United States and around the world. The present invention also provides for effective humectant compositions formed in accordance with the method described above, as well as treated soils including an effective amount of humectant composition applied thereto. An effective amount of humectant composition, as provided herein, is from the minimum humectant concentration level (i.e., greater than 0 parts when the minimum humectant concentration level is zero, or at the minimum humectant concentration level wherein the minimum humectants concentration level is not zero) to 86.5 parts per million parts of soil.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on.

As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The following examples are intended to illustrate the invention and are not to be viewed as limiting to the invention.

Examples

1. Preparation and Composition of Humectants According to the Formula $(Y[Z_a(CH_2CH_2O)_b(CH_2CH(CH_3)O)_cH]_x)$ or $[Z_a(CH_2CH_2O)_b(CH_2CH(CH_3)O)_c(CH_2CH(Ph)O)_dH]_x$ In general, the method for preparing polyol compositions according to the formula $Y[Z_a(CH_2CH_2O)_b(CH_2CH(CH_3)O)_cH]_x$ or $Y[Z_a(CH_2CH_2O)_b(CH_2CH(CH_3)O)_c(CH_2CH(Ph)O)_d(Ph)O)_dH]_x$ is as follows. First, a molecule (i.e., an organic compound) with reactive OH units was introduced into a reactor. To make the Z (heteric) portion of the new molecule, ethylene oxide (EO), and/or propylene oxide (PO) and/or butylene oxide (BO) and/or styrene oxide (SO) were then introduced into the reactor at the same time at the desired inclusion rates of each one individually. These molecules were reacted in a random order via an alkoxylation reaction to produce a larger molecule with reactive OH units. Once this molecule is formed, EO or PO or SO were introduced into the reactor (but not at the same time) to produce a molecule that had blocks of repeating EO or PO or SO units. The EO or PO or SO was introduced into the reactor until the desired size (molecular weight) of the final molecule was achieved.

Specific test samples A-I formed in accordance with the general method are provided in Table 2 below, with all % described below being the total weight percent of the respective component (% Initiator, % $Z_a$, % $(EO)_b$, % $(PO)_c$, % $(SO)_d$) in the formed Sample. In addition, all $M_w$ listed in Table 2 for Samples A-I are weight average molecular weights and are rounded to the nearest 100.

TABLE 2

| Sample | Initiator | % $Z_a$ (with % EO, PO, BO, and SO) | % $(EO)_b$ | % $(PO)_c$ | % $(SO)_d$ | $M_w$ |
|---|---|---|---|---|---|---|
| A | 3% glycerol | 87% - (10, 77, 0, 0) | 0 | 10 | 0 | 3000 |
| B | 3% glycerol | 87% - (12.5, 74.5, 0, 0) | 0 | 10 | 0 | 3000 |
| C | 3% glycerol | 87% - (25, 62, 0, 0) | 0 | 10 | 0 | 3000 |
| D | 10% Naphthol | 0 | 90 | 0 | 0 | 1500 |
| E | 5% Naphthol | 0 | 95 | 0 | 0 | 3000 |
| F | 3% glycerol | 97% - (12, 85, 0, 0) | 0 | 0 | 0 | 2800 |
| G | 5% Naphthol | 0 | 85 | 10 | 0 | 3000 |
| H | 2.5% glycerol | 97.5% - (73, 24.5, 0, 0) | 0 | 0 | 0 | 3600 |
| I | 3.5% Diethylene glycol | 0 | 86.5 | 0 | 10 | 3000 |

2. Preparation of Sample J (a Graft Polyol Dispersion with 15% Polyacrylic Acid Homopolymer Dispersed in the Polyether Polyol of Sample H)

In general, a method for forming Sample J is as follows. First, Sample H (the polyether polyol as shown Table 2 above), acrylic acid, a macromer, a reaction moderator, and a free radical polymerization initiator were introduced into the reactor at the same time. The acrylic acids, macromer, and reaction moderator then reacted in the presence of a free radical polymerization initiator and heat and Sample H. The graft polyol dispersion formed, Sample J, included 15% by weight of the polyacrylic acid homopolymer dispersed in Sample H.

3. Preparation of Soil Samples—in General

Soil samples were broken up by hand then sieved through a #10 sieve (0.0787 Inch mesh opening.) Water content of the soil was determined with a 105° C. moisture balance, so that the amount of humectant in soil was based on the dry weight of soil. 2000, 5000, and 8000 ppm solutions of the polyol compositions from Table 1 in deionized water were then prepared.

Next, 1.25 grams of the humectant composition (Samples A-J) was added to a plastic container containing 437.5 grams of soil (based on dry weight) and the mixture was then tumbled for at minimum of 30 minutes. The mixed soil and humectant solution were then sifted at least twice through a #10 sieve to break up any agglomerations. The samples were then stored in closed plastic containers until needed for use.

Homogenous samples of treated and untreated soils were placed in 16×50 mm open Petri dishes. These Petri dishes were placed on shelves in sealed large plastic containers. The plastic containers and the under sides of the shelves were lined with filter paper. The filter paper was moistened with deionized water and a small fan was introduced into the plastic container to insure air circulation. One more piece of filter paper was placed on the exit side of the fan, its size being large enough so that it touches the bottom of the plastic container. After the Petri dishes were placed on the shelves, deionized water was poured onto the bottom of the plastic container to act as a water reservoir, as the filter paper was wet out by capillary action. The Petri dishes with samples were left in the plastic container for a minimum of 7 days before being tested.

4. Evaluation of Samples

Moisture contents of the soil samples were measured on two Mettler moisture balances. One moisture balance dried a 3.1 to 3.2 gram sample of soil at a 40° C. isothermal temperature to a number 4 set point. The other moisture balance dried a 5.3 to 5.4 gram sample of soil at 105° C. isothermal temperature to a number 3 set point. A maximum of 7 samples were run for each combination of soil, humectant and humectant level, with the number of runs varied depending on the density of soil and the amount of sample available. The ambient temperature and relative humidity were measured at the onset of each test run.

The results from the moisture balance work were analyzed using JMP statistical analysis software commercially available from SAS Institute of Cary, N.C.

Results were analyzed for each combination of soil type and humectant. The first step was to use the multivariant analysis to remove outlier data points with a Mahalanobis value of 4 or higher. Next, the JMP software was allowed to break the moisture content data down into individual contributions based on ambient temperature, temperature of the moisture balance, relative humidity, and concentration level of the humectant in the respective samples. For this technique, the Fit Model analysis was used and treated moisture values as the Y-value, while humectant concentration level, ambient temperature, relative humidity, and temperature of the moisture balance was treated as the model effects. For this analysis, the model effects were considered linear with no cross terms or powers. The model was chosen to be a standard least squares fit with an intercept.

It was necessary to include ambient temperature and relative humidity into the JMP analysis, because moisture determinations were carried out in a laboratory where temperature and humidity varied a great deal depending on the weather conditions. The Prediction Profiler in the JMP software was used exclusively as the predictor for average moisture value based on all the modeling effects. A p value of 0.05 or less was the cut off for determining statistical significance of any of the modeling effects. A 0.05 p value means that if the experiments were repeated 20 times, it would be expected that in 19 of those times the average value of moisture content would fall within the upper and lower limits of error bars illustrated numerically on the left side of the graph if the modeling effects were held constant at any level within the design space. The results of each of the samples are summarized in Table 3 below with respect to each of Samples A-J on each of the four representative soil types (Dinuba, Los Banos, Lubbock, and Nebraska). Accompanying Fit Model analysis graphs that confirm the measurements for each soil sample are graphically illustrated in FIGS. 1-20 and include plots illustrating the average slope curve 25 and upper and lower error limits 30, 35 for each sample as summarized in Table 3 below:

TABLE 3

| Sample | Soil Type | Average Moisture Content at 0 ppm | Average Moisture Content at 86.5 ppm | Predicted Average Slope Value from 0 to 86.5 ppm | P Value | Effective as Humectant in Soil Type? | Effective as Humectant for 3 of 4 soil types? |
|---|---|---|---|---|---|---|---|
| A | Dinuba 40° C. | 2.60 | 2.44 | −.0019 | .1159 | No | |
| A | Dinuba 105° C. | 3.55 | 3.39 | −.0019 | .1159 | No | |
| A | Los Banos 40° C. | 6.95 | 6.45 | −.0059 | .0059 | No | |
| A | Los Banos 105° C. | 9.89 | 9.38 | −.0059 | .0059 | No | |
| A | Lubbock 40° C. | 5.13 | 5.72 | .0068 | <.0001 | Yes | |
| A | Lubbock 105° C. | 7.37 | 7.96 | .0068 | <.0001 | Yes | |
| A | Nebraska 40° C. | 8.91 | 9.06 | .0018 | .6127 | No | |
| A | Nebraska 105° C. | 11.72 | 11.88 | .0018 | .6127 | No | |
| A | Summary | | | | | | No |
| B | Dinuba 40° C. | 2.47 | 2.74 | .0031 | .0004 | Yes | |
| B | Dinuba 105° C. | 3.38 | 3.65 | .0031 | .0004 | Yes | |
| B | Los Banos 40° C. | 6.71 | 6.30 | −.0047 | .054 | No | |
| B | Los Banos 105° C. | 9.68 | 9.27 | −.0047 | .054 | No | |
| B | Lubbock 40° C. | 5.42 | 5.87 | .0052 | <.0001 | Yes | |
| B | Lubbock 105° C. | 7.60 | 8.05 | .0052 | <.0001 | Yes | |
| B | Nebraska 40° C. | 8.65 | 9.18 | .0061 | .0005 | Yes | |
| B | Nebraska 105° C. | 11.50 | 12.03 | .0061 | .0005 | Yes | |
| B | Summary | | | | | | Yes |
| C | Dinuba 40° C. | 2.44 | 2.87 | .0049 | <.0001 | Yes | |
| C | Dinuba 105° C. | 3.32 | 3.75 | .0049 | <.0001 | Yes | |
| C | Los Banos 40° C. | 6.82 | 5.94 | −.0101 | .0048 | No | |

TABLE 3-continued

| Sample | Soil Type | Average Moisture Content at 0 ppm | Average Moisture Content at 86.5 ppm | Predicted Average Slope Value from 0 to 86.5 ppm | P Value | Effective as Humectant in Soil Type? | Effective as Humectant for 3 of 4 soil types? |
|---|---|---|---|---|---|---|---|
| C | Los Banos 105° C. | 9.63 | 8.76 | −.0101 | .0048 | No | |
| C | Lubbock 40° C. | 5.17 | 5.12 | −.0006 | .6350 | No | |
| C | Lubbock 105° C. | 7.60 | 7.54 | −.0006 | .6350 | No | |
| C | Nebraska 40° C. | 9.19 | 9.13 | −.0007 | .6298 | No | |
| C | Nebraska 105° C. | 12.07 | 12.01 | −.0007 | .6298 | No | |
| C | Summary | | | | | | No |
| D | Dinuba 40° C. | 2.50 | 2.79 | .0033 | <.0001 | Yes | |
| D | Dinuba 105° C. | 3.50 | 3.79 | .0033 | <.0001 | Yes | |
| D | Los Banos 40° C. | 6.67 | 7.02 | .0040 | .0350 | Yes | |
| D | Los Banos 105° C. | 9.64 | 9.99 | .0040 | .0350 | Yes | |
| D | Lubbock 40° C. | 5.32 | 5.21 | −.0013 | .3399 | No | |
| D | Lubbock 105° C. | 7.62 | 7.50 | −.0013 | .3399 | No | |
| D | Nebraska 40° C. | 8.39 | 8.14 | −.0029 | .4978 | No | |
| D | Nebraska 105° C. | 11.23 | 10.98 | −.0029 | .4978 | No | |
| D | Summary | | | | | | No |
| E | Dinuba 40° C. | 2.58 | 2.86 | .0031 | <.0001 | Yes | |
| E | Dinuba 105° C. | 3.53 | 3.80 | .0013 | <.0001 | Yes | |
| E | Los Banos 40° C. | 7.03 | 7.25 | .0025 | .1309 | No | |
| E | Los Banos 105° C. | 10.06 | 10.28 | .0025 | .1309 | No | |
| E | Lubbock 40° C. | 4.94 | 6.16 | .0140 | <.0001 | Yes | |
| E | Lubbock 105° C. | 7.04 | 8.26 | .0140 | <.0001 | Yes | |
| E | Nebraska 40° C. | 7.94 | 8.92 | .0113 | .0062 | Yes | |
| E | Nebraska 105° C. | 10.76 | 11.74 | .0113 | .0062 | Yes | |
| E | Summary | | | | | | Yes |
| F | Dinuba 40° C. | 3.27 | 3.97 | 0.0081 | <.0001 | Yes | |
| F | Dinuba 105° C. | 4.08 | 4.78 | 0.0081 | <.0001 | Yes | |
| F | Los Banos 40° C. | 9.38 | 10.06 | 0.0079 | <.0001 | Yes | |
| F | Los Banos 105° C. | 11.97 | 12.65 | 0.0079 | <.0001 | Yes | |
| F | Lubbock 40° C. | 6.66 | 6.96 | 0.0035 | 0.035 | Yes | |
| F | Lubbock 105° C. | 8.50 | 8.80 | 0.0035 | 0.035 | Yes | |
| F | Nebraska 40° C. | 9.48 | 11.48 | 0.0231 | <.0001 | Yes | |
| F | Nebraska 105° C. | 11.61 | 13.61 | 0.0231 | <.0001 | Yes | |
| F | Summary | | | | | | Yes |
| G | Dinuba 40° C. | 2.94 | 4.39 | 0.0168 | <.0001 | Yes | |
| G | Dinuba 105° C. | 3.69 | 5.14 | 0.0168 | <.0001 | Yes | |
| G | Los Banos 40° C. | 8.89 | 10.58 | 0.0195 | <.0001 | Yes | |
| G | Los Banos 105° C. | 11.46 | 13.15 | 0.0195 | <.0001 | Yes | |
| G | Lubbock 40° C. | 6.43 | 7.18 | 0.0087 | 0.0001 | Yes | |

TABLE 3-continued

| Sample | Soil Type | Average Moisture Content at 0 ppm | Average Moisture Content at 86.5 ppm | Predicted Average Slope Value from 0 to 86.5 ppm | P Value | Effective as Humectant in Soil Type? | Effective as Humectant for 3 of 4 soil types? |
|---|---|---|---|---|---|---|---|
| G | Lubbock 105° C. | 8.49 | 9.24 | 0.0087 | 0.0001 | Yes | |
| G | Nebraska 40° C. | 9.36 | 12.38 | 0.0349 | <.0001 | Yes | |
| G | Nebraska 105° C. | 11.53 | 14.55 | 0.0349 | <.0001 | Yes | |
| G | Summary | | | | | | Yes |
| H | Dinuba 40° C. | 3.24 | 3.27 | 0.0003 | 0.6068 | No | |
| H | Dinuba 105° C. | 3.96 | 4.00 | 0.0003 | 0.6068 | No | |
| H | Los Banos 40° C. | 9.15 | 12.30 | 0.0364 | <.0001 | Yes | |
| H | Los Banos 105° C. | 11.70 | 14.85 | 0.0364 | <.0001 | Yes | |
| H | Lubbock 40° C. | 6.70 | 8.43 | 0.0200 | <.0001 | Yes | |
| H | Lubbock 105° C. | 8.53 | 10.26 | 0.0200 | <.0001 | Yes | |
| H | Nebraska 40° C. | 9.03 | 8.91 | −0.0014 | 0.4820 | No | |
| H | Nebraska 105° C. | 11.16 | 11.04 | −0.0014 | 0.4820 | No | |
| H | Summary | | | | | | No |
| I | Dinuba 40° C. | 2.80 | 3.12 | 0.0037 | <.0001 | Yes | |
| I | Dinuba 105° C. | 3.72 | 4.04 | 0.0037 | <.0001 | Yes | |
| I | Los Banos 40° C. | 8.43 | 9.96 | 0.0177 | <.0001 | Yes | |
| I | Los Banos 105° C. | 11.29 | 12.82 | 0.0177 | <.0001 | Yes | |
| I | Lubbock 40° C. | 5.97 | 6.63 | 0.0076 | <.0001 | Yes | |
| I | Lubbock 105° C. | 8.22 | 8.89 | 0.0076 | <.0001 | Yes | |
| I | Nebraska 40° C. | 8.51 | 9.39 | 0.0102 | 0.0014 | Yes | |
| I | Nebraska 105° C. | 11.11 | 11.99 | 0.0102 | 0.0014 | Yes | |
| I | Summary | | | | | | Yes |
| J | Dinuba 40° C. | 2.92 | 3.82 | 0.0104 | <.0001 | Yes | |
| J | Dinuba 105° C. | 3.83 | 4.74 | 0.0104 | <.0001 | Yes | |
| J | Los Banos 40° C. | 8.58 | 10.14 | 0.0180 | <.0001 | Yes | |
| J | Los Banos 105° C. | 11.50 | 13.06 | 0.0180 | <.0001 | Yes | |
| J | Lubbock 40° C. | 5.76 | 6.38 | 0.0072 | <.0001 | Yes | |
| J | Lubbock 105° C. | 8.16 | 8.77 | 0.0072 | <.0001 | Yes | |
| J | Nebraska 40° C. | 8.74 | 12.29 | 0.0410 | <.0001 | Yes | |
| J | Nebraska 105° C. | 11.32 | 14.86 | 0.0410 | <.0001 | Yes | |
| J | Summary | | | | | | Yes |

As Table 3 and corresponding FIGS. 1-20 illustrate, Samples B, E, F, G, I and J were considered "effective humectant compositions" for use in all representative soils as determined by the method of the present invention because they provided a increasing slope value along the length of the average slope curve 25 from 0 to 86.5 ppm of humectant composition in the soil sample and because the average p value for these samples was less than 0.05 for at least three of the soil types tested. Conversely, Samples A, C, D, and H, while each considered "effective humectant compositions" in certain of the representative soils, were deemed "not effective" for use in all representative soils by the provided method because they did not provide both a increasing slope value along the length of the average slope curve 25 from 0 to 86.5 ppm of humectant composition in the soil sample and an average p value of less than 0.05 for at least three of the soil types tested.

The instant disclosure has been described in an illustrative manner, and it is to be understood that the terminology which has been used is intended to be in the nature of words of description rather than of limitation. Many modifications and variations of the instant disclosure are possible in light of the above teachings. It is, therefore, to be understood that within the scope of the appended claims, the instant disclosure may be practiced otherwise than as specifically described.

The invention claimed is:

1. A humectant composition for increasing moisture retention in a soil, the humectant composition consists of a composition of the formula $$Y[Z_a(CH_2CH_2O)_b(CH_2CH(CH_3)O)_cH]_x,$$

wherein
Y is derived from an organic compound having x reactive hydroxyl groups;
Z represents a heteric copolymer derived from the alkoxylation reaction product of ethylene oxide and propylene oxide,
the subscript a is a positive number,
the subscript b is zero or a positive number,
the subscript c is zero or a positive number, and
the subscript x is one or greater; and
wherein the weight average molecular weight of the composition ranges from 2000 to 6000 g/mol,
wherein the composition comprises the reaction product of:
(i) 3% by weight of a trifunctional alcohol,
(ii) 10 to 15% by weight of ethylene oxide, and
(iii) 82 to 87% by weight of propylene oxide,
or the reaction product of:
(i) 3 to 8% by weight of a monofunctional alcohol or difunctional alcohol,
(ii) 82 to 87% by weight of ethylene oxide, and
(iii) more than 0 and up to 10% by weight of propylene oxide,
wherein said humectant composition provides an increasing average moisture content of the soil to which it is applied along an entirety of a length of an average slope curve from a minimum humectant concentration level to a maximum humectant concentration level,
wherein said average slope curve is determined by plotting an average moisture content of said soil having said humectant composition applied thereon at concentration levels from the minimum humectant concentration level to the maximum humectant concentration level, and
wherein said average slope curve has a p value of 0.05 or less.

2. The humectant composition according to claim 1, wherein the humectant composition provides the increasing average moisture content along the entirety of the length of the average slope curve from the minimum humectant concentration level to the maximum humectant concentration level on at least three soils selected from the group consisting of Dinuba soil, Los Banos soil, Lubbock soil, and Nebraska soil, and
wherein the generated average slope curve on the at least three soils selected from the group consisting of Dinuba soil, Los Banos soil, Lubbock soil, and Nebraska soil has a p value of 0.05 or less.

3. The humectant composition according to claim 1, wherein the weight average molecular weight of the composition ranges from 2700 to 3300 g/mol.

4. The humectant composition according to claim 1, wherein Y is derived from a mixture of at least two organic compounds having a different number of reactive hydroxyl groups.

5. The humectant composition according to claim 1, wherein Y is derived from an organic compound having one reactive hydroxyl group.

6. The humectant composition according to claim 1, wherein Y is derived from an organic compound having more than one reactive hydroxyl group.

7. The humectant composition according to claim 1, wherein $(CH_2CH(CH_3)O)_c$ is present and comprises at most 10% by weight of the total weight of the composition.

8. The humectant composition according to claim 1, wherein the composition comprises the reaction product of:
(i) 3% by weight of a trifunctional alcohol,
(ii) 10 to 15% by weight of ethylene oxide, and
(iii) 82 to 87% by weight of propylene oxide,
wherein the % by weight of components (i)-(iii) is based upon the total weight of the composition; and
wherein $(CH_2CH(CH_3)O)_c$ is present and comprises at most 10% by weight of the total weight of the composition.

9. A treated soil comprising:
soil; and
a humectant composition according to claim 1 applied on the soil in an amount ranging from greater than 0 parts to 86.5 parts of the humectant composition per million parts of the soil.

10. The humectant composition according to claim 1, wherein the subscript b is zero.

11. The humectant composition according to claim 1, wherein the subscript b is zero and wherein the subscript c is zero.

12. The treated soil according to claim 9, wherein the subscript b is zero.

13. The treated soil according to claim 9, wherein the subscript b is zero and wherein the subscript c is zero.

14. A humectant composition for increasing moisture retention in a soil, the humectant composition consists of a composition of the formula $$Y[Z_a(CH_2CH_2O)_b(CH_2CH(CH_3)O)_cH]_x,$$

wherein
Y is derived from an organic compound having one reactive hydroxyl group;
Z represents a heteric copolymer derived from the alkoxylation reaction product of ethylene oxide and propylene oxide,
the subscript a is a positive number,
the subscript b is zero or a positive number, and
the subscript c is zero or a positive number; and
wherein the composition comprises the reaction product of:
(i) 3 to 8% by weight of a monofunctional alcohol,
(ii) 82 to 87% by weight of ethylene oxide, and
(iii) more than 0 and up to 10% by weight of propylene oxide,
wherein said humectant composition provides an increasing average moisture content of the soil to which it is applied along an entirety of a length of an average slope curve from a minimum humectant concentration level to a maximum humectant concentration level,
wherein said average slope curve is determined by plotting an average moisture content of said soil having said humectant composition applied thereon at concentration levels from the minimum humectant concentration level to the maximum humectant concentration level, and
wherein said average slope curve has a p value of 0.05 or less.

15. A treated soil comprising:

soil; and a humectant composition applied on said soil in an amount ranging from greater than 0 parts to 86.5 parts of said humectant composition per million parts of said soil, said humectant composition consists of a composition of the formula $Y[Z_a(CH_2CH_2O)_b(CH_2CH(CH_3)O)_cH]_x$, wherein Y is derived from an organic compound having x reactive hydroxyl groups;

Z represents a heteric copolymer derived from the alkoxylation reaction product of ethylene oxide and propylene oxide, the subscript a is a positive number, the subscript b is zero or a positive number, the subscript c is zero or a positive number, and the subscript x is one or greater, wherein the composition comprises the reaction product of:

(i) 3% by weight of a trifunctional alcohol, (ii) 10 to 15% by weight of ethylene oxide, and (iii) 82 to 87% by weight of propylene oxide, or the reaction product of:

(i) 3 to 8% by weight of a monofunctional alcohol or difunctional alcohol, (ii) 82 to 87% by weight of ethylene oxide, and (iii) more than 0 and up to 10% by weight of propylene oxide, wherein said humectant composition provides an increasing average moisture content of the treated soil along an entirety of a length of an average slope curve as said amount of said humectant composition increases from greater than 0 parts to 86.5 parts, wherein said average slope curve is determined by plotting an average moisture content of said soil having said humectant composition applied thereon at said amounts ranging from greater than 0 parts to 86.5 parts, and wherein said average slope curve has a p value of 0.05 or less.

* * * * *